US011813194B2

(12) United States Patent
Diller et al.

(10) Patent No.: US 11,813,194 B2
(45) Date of Patent: Nov. 14, 2023

(54) WATER PERFUSION HEAT EXCHANGE PAD FOR CONTROL OF SKIN TEMPERATURE

(71) Applicant: BOARD OF REGENTS, THE UNIVERSITY OF TEXAS SYSTEM, Austin, TX (US)

(72) Inventors: Kenneth R. Diller, Elgin, TX (US); Gary L. McGregor, Pflugerville, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 697 days.

(21) Appl. No.: 16/491,773

(22) PCT Filed: Mar. 6, 2018

(86) PCT No.: PCT/US2018/021038
§ 371 (c)(1),
(2) Date: Sep. 6, 2019

(87) PCT Pub. No.: WO2018/165086
PCT Pub. Date: Sep. 13, 2018

(65) Prior Publication Data
US 2020/0383825 A1 Dec. 10, 2020

Related U.S. Application Data

(60) Provisional application No. 62/467,294, filed on Mar. 6, 2017.

(51) Int. Cl.
*A61F 7/02* (2006.01)
*A61F 7/00* (2006.01)
(52) U.S. Cl.
CPC ........ *A61F 7/02* (2013.01); *A61F 2007/0054* (2013.01); *A61F 2007/0056* (2013.01); *A61F 2007/0225* (2013.01)

(58) Field of Classification Search
CPC ...... A61F 2007/0054; A61F 2007/0056; A61F 7/02; A61F 2007/0225
See application file for complete search history.

(56) References Cited

U.S. PATENT DOCUMENTS 5,417,720 A * 5/1995 Mason ................ A61M 5/1415
607/104
6,238,428 B1 5/2001 Werneth et al.
(Continued)

FOREIGN PATENT DOCUMENTS

CA 2880888 2/2014
WO 9640331 12/1996
(Continued)

OTHER PUBLICATIONS

Agache et al., Mechanical properties and Young's modulus of human skin in vivo, Arch. Dermatol. Res. 269(3), 221-232 (1980).
(Continued)

*Primary Examiner* — Kaitlyn E Smith
*Assistant Examiner* — Bradford C. Blaise
(74) *Attorney, Agent, or Firm* — Meunier Carlin & Curfman LLC

(57) ABSTRACT

Heat exchange pads for use on a patient are described herein. An example heat exchange pad can include a surface defining an internal volume and having a flexible patient contacting portion, an inlet fluidly connected to the internal volume for delivery of fluid into the internal volume, an outlet fluidly connected to the internal volume for removal of fluid from the internal volume, and at least one extended surface structure positioned within the internal volume to disrupt laminar flow of fluid from the inlet to the outlet.

20 Claims, 15 Drawing Sheets

(56) References Cited

U.S. PATENT DOCUMENTS

| | | | |
|---|---|---|---|
| 6,371,976 B1* | 4/2002 | Vrzalik | A61F 7/0097 607/104 |
| 6,599,312 B2 | 7/2003 | Dobak, III | |
| 7,001,417 B2 | 2/2006 | Elkins | |
| 2003/0213580 A1* | 11/2003 | Philpott | F28F 21/065 29/890.032 |
| 2003/0229385 A1* | 12/2003 | Elkins | A61F 7/0085 607/104 |
| 2006/0111764 A1* | 5/2006 | Kirkman | A61F 7/12 607/104 |
| 2006/0191675 A1 | 8/2006 | Fletcher | |
| 2007/0068651 A1* | 3/2007 | Gammons | A61F 7/02 607/108 |
| 2009/0312823 A1 | 12/2009 | Patience et al. | |
| 2011/0238051 A1 | 9/2011 | Levinson et al. | |
| 2012/0109232 A1 | 5/2012 | Mohn | |
| 2013/0116760 A1 | 5/2013 | Carson et al. | |
| 2013/0296981 A1* | 11/2013 | Saggers | A61F 7/0085 607/104 |
| 2014/0155964 A1* | 6/2014 | Saggers | A61F 7/0097 607/104 |
| 2014/0214138 A1* | 7/2014 | Voorhees | A61F 7/10 607/104 |
| 2014/0228718 A1 | 8/2014 | Diller et al. | |
| 2014/0371732 A1 | 12/2014 | Rose | |
| 2016/0376486 A1* | 12/2016 | Atieh | F28F 23/00 165/104.19 |
| 2017/0128258 A1 | 5/2017 | Diller et al. | |

FOREIGN PATENT DOCUMENTS

| | | |
|---|---|---|
| WO | 2006110405 | 10/2006 |
| WO | 2017223417 | 12/2017 |

OTHER PUBLICATIONS

Ahmed et al., An overview on heat transfer augmentation using vortex generators and nanofluids: approaches and applications, Renew. Sustain. Energy Rev. 16, 5951-5993 (2012).

Al-Rjoub et al., Enhanced heat transfer in a micro-scale heat exchanger using nano-particle laden electro-osmotic flow, Intl. Comm. Heat Mass Trans. 68, 228-235 (2015).

Biswas et al., Heat transfer enhancement in fin-tube heat exchangers by winglet type vortex generators, Intl. J. Heat Mass Trans. 37(2), 283-291 (1994).

Caldwell et al., Three-dimensional interactions of mean body and local skin temperatures in the control of hand and foot blood flows, Eur. J. Appl. Physiol. 114, 1679-1689 (2014).

Christmas et al., Sustained cutaneous vasoconstriction during and following cyrotherapy treatment: role of oxidative stress and Rho kinase. Microvascular research. Jul. 1, 2016;106:96-100.

Diller, Modeling of bioheat transfer processes at high and low temperatures, Advances Heat Transfer 22, 157-357 (1992).

Diller, Therapeutic Recruitment of Thermoregulation in Humans by Selective Thermal Stimulation Along the Spine, Advances Heat Transfer 47, 341-396, doi.org/10.1016/bs.aiht.2015.08.002 (2015).

Diller, Heat transfer in health and healing (Max Jakob Award paper), J. Heat Transfer, 137(10), 102401.1-11. doi: 10.1115/1.4030565 (2015).

Diller et al., Effects of Cold Temperature on the Skin, in Dermatological Cryosurgery and Cryotherapy, ed. by Abramovits, W., Graham, G., Har-Shai, Y. and Strumia, R., Springer Press, 2016, 39-43.

Dixit et al., Review of micro- and mini-channel heat sinks and heat exchangers for single phase fluids, Renew. Sustain. Energy Rev. 41, 1298-1311 (2015).

Falanga et al., Use of a durometer to assess skin hardness, J. Amer. Acad. Dermatol. 29(1), 47-51 (1993).

Haller et al., Simulation and experimental investigation of pressure loss and heat transfer in microchannel networks containing bends and T-junctions, Intl. J. Heat Mass Trans. 52(11-12), 2678-2689 (2009).

Hassanipour et al., Preliminary experimental study of a bio-inspired, phase-change particle capillary heat exchanger, Intl. J. Heat Mass Trans. 53, 3300-3307 (2010).

He et al., Convective heat transfer enhancement: mechanisms, techniques, and performance evaluation, Advances Heat Transfer 46, 87-186 (2014).

He et al., Advances and outlooks of heat transfer enhancement by longitudinal vortex generators, Advances Heat Transfer 44, 119-185 (2012).

Heller et al., Enhancing thermal exchange in humans and practical applications, Disruptive Sci. Tech. 1(1), 11-19 (2012).

Kandlikar, History, advances, and challenges in liquid flow and flow boiling heat transfer in microchannels: a critical review, J. Heat Trans. 134, 034001:1-15 (2012).

Kandlikar et al., Heat transfer in microchannels—2012 status and research needs, J. Heat Trans. 135, 091001:1-18 (2013).

Kandlikar et al., Heat Transfer and Fluid Flow in Minichannels and Microchannels, Second Ed., Elsevier, Waltham (2014).

Khoshnevis et al., Experimental Characterization of the Domains of Coupling and Uncoupling Between Surface Temperature and Skin Blood Flow, International Journal of Transport Phenomena 13, 2014, 277-301.

Khoshnevis S et al., Quantitative Evaluation of the Thermal Heterogeneity on the Surface of Cryotherapy Cooling Pads, J. Biomech. Engr. 136, 2014, 074503, 1-7.

Khoshnevis et al., Cold-Induced Vasoconstriction May Persist Long After Cooling Ends: an Evaluation of Multiple Cryotherapy Units, Knee Surgery, Sports Traumatology, Arthroscopy 23(9), 2015, 2475-2483.

Khoshnevis et al., Cryotherapy-Induced Persistent Vasoconstriction after Cutaneous Cooling: Hysteresis between Skin Temperature and Blood Perfusion, J. Biomech. Engr.138(3), 2016, 031004-1-8.

Khoshvaght-Aliabadi et al., Performance of a plate-fin heat exchanger with vortex-generator channels: 3D-CFD simulation and experimental validation, Intl. J. Thermal Sci. 88, 180-192 (2015).

Kockmann et al., Transitional flow and related transport phenomena in curved microchannels, Heat Trans. Engr. 32(7-8), 595-608 (2011).

Mejia et al., An On-Site Thermoelectric Cooling Device for Cryotherapy and Control of Skin Blood Flow, J. Medical Devices 9(4), 2015, 044502, 1-6.

Pailler-Mattei et al., In vivo measurement of the elastic mechanical properties of human skin by indentation tests, Med. Engr. Physics 30(5), 599-606 (2008).

Sengupta et al., A review on the mechanical and electrical properties of graphite and modified graphite reinforced polymer composites, Prog. Polymer Sci. 36, 638-670 (2011).

Taylor et al., Hands and feet: physiological insulators, radiator and evaporators, Eur. J. Appl. Physiol. 114(10), 2037-1060 (2014).

Tullius et al., A review of cooling in microchannels, Heat Trans. Engr. 32(7-8), 527-541 (2011).

Walloe, Arterio-venous anastomoses in the human skin and their role in temperature control, Temperature 3(1), 92-103 (2016).

Wang et al., In situ polymerization of grapheme nanosheets and polyurethane with enhanced mechanical and thermal properties, J. Mater. Chem. 21, 4222-42 (2011).

Yu et al., Enhanced thermal conductivity in a hybrid graphite nanoplatelet—carbon nanotube filler for epoxy composites, Adv. Mater. 20, 4740-4722-4727 (2008).

Grant et al., Observation on arteriovenous anastomoses in human skin and in the birds foot with special references to the reaction to cold, Heart 15, 385-411 (1931).

Molyneux et al., Comparative aspects of arteriovenous anastomoses, Prog. Anatomy 1, 207-228 (1981).

International Search Report and Written Opinion dated May 25, 2018, from International Application No. PCT/US2018/021038, 8 pages.

* cited by examiner

PRIOR ART

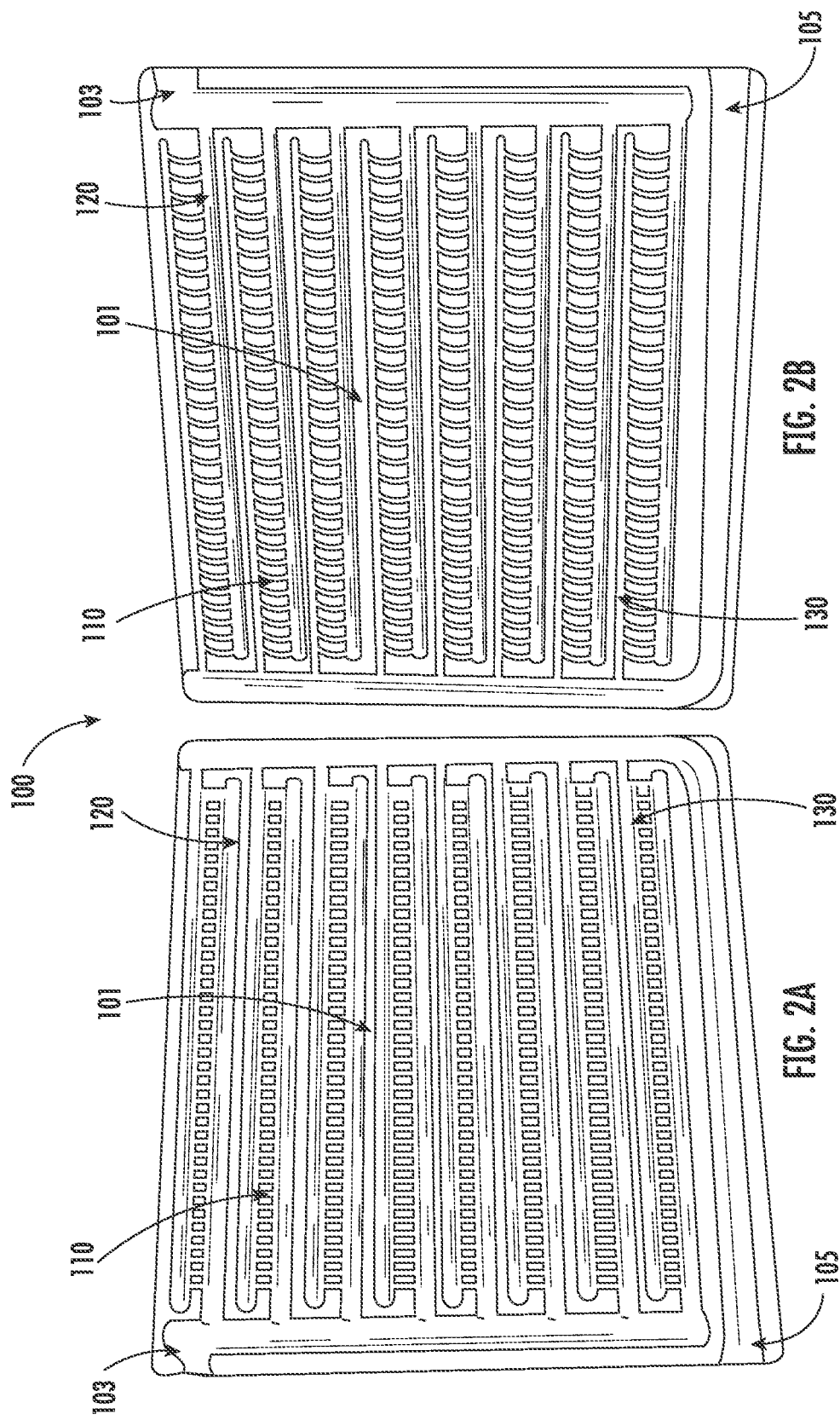

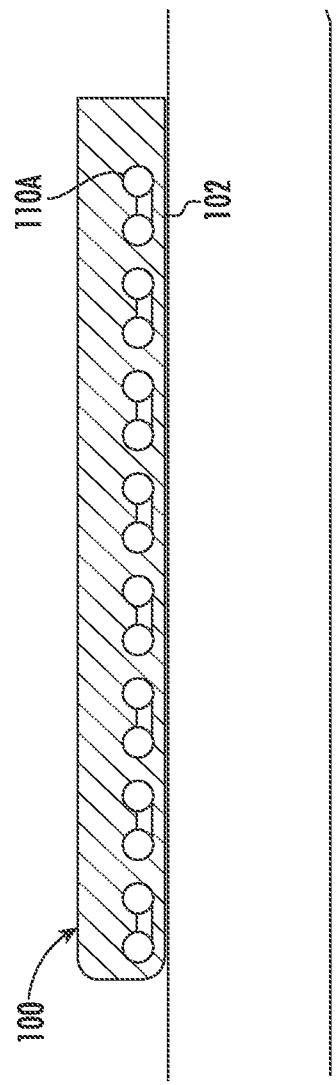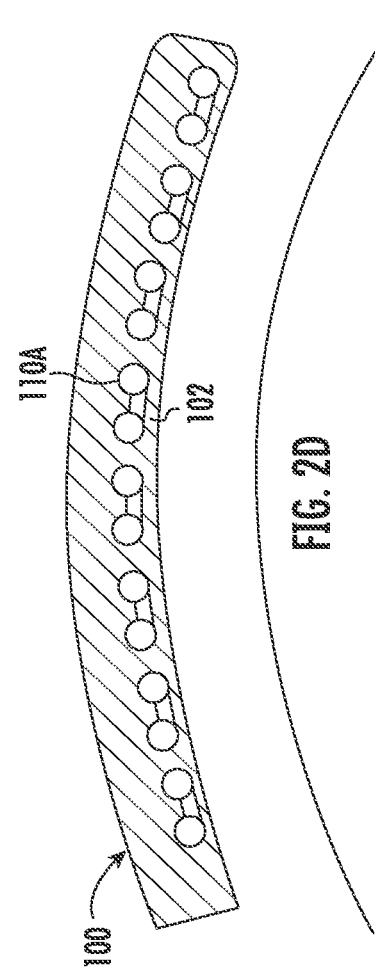

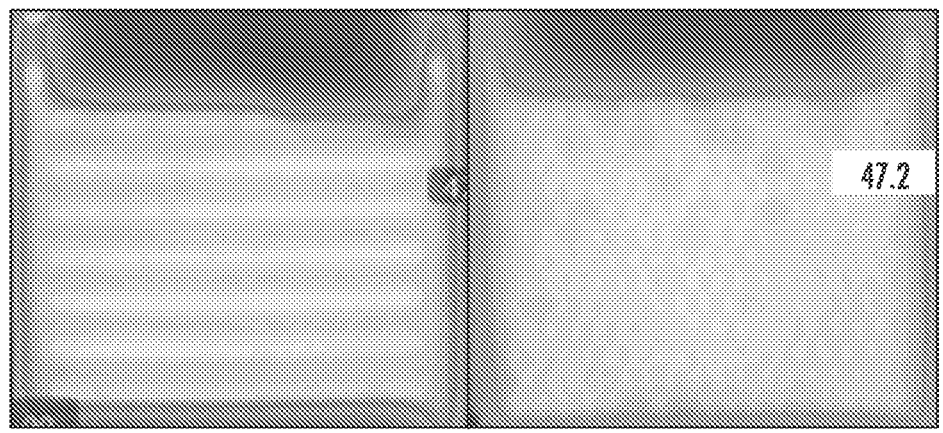
FIG. 6A             FIG. 6B
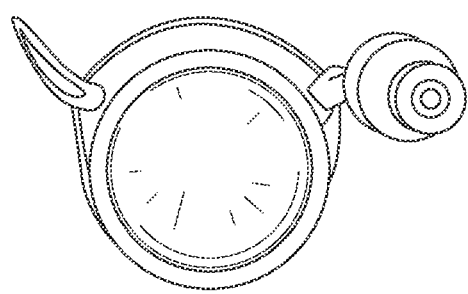     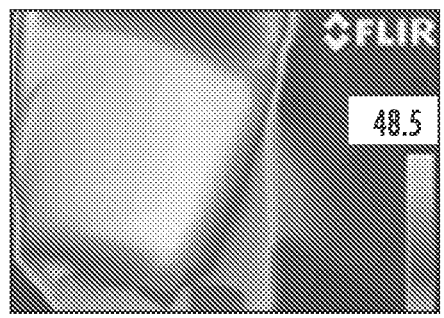
FIG. 7A             FIG. 7B

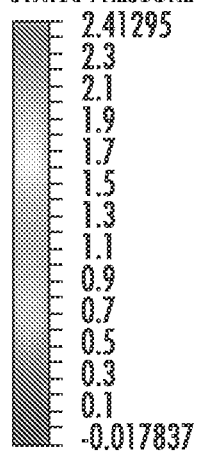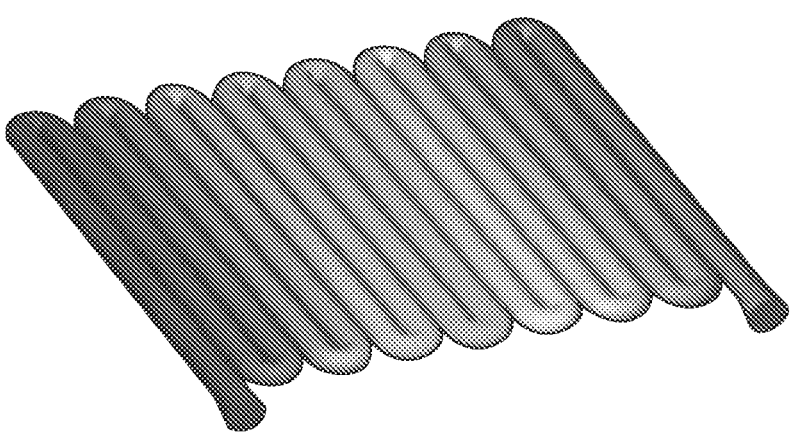
FIG. 10A
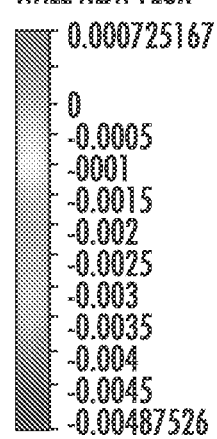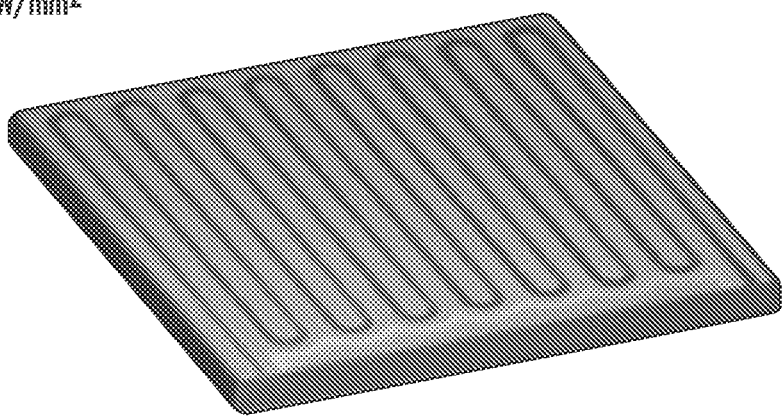
FIG. 10B

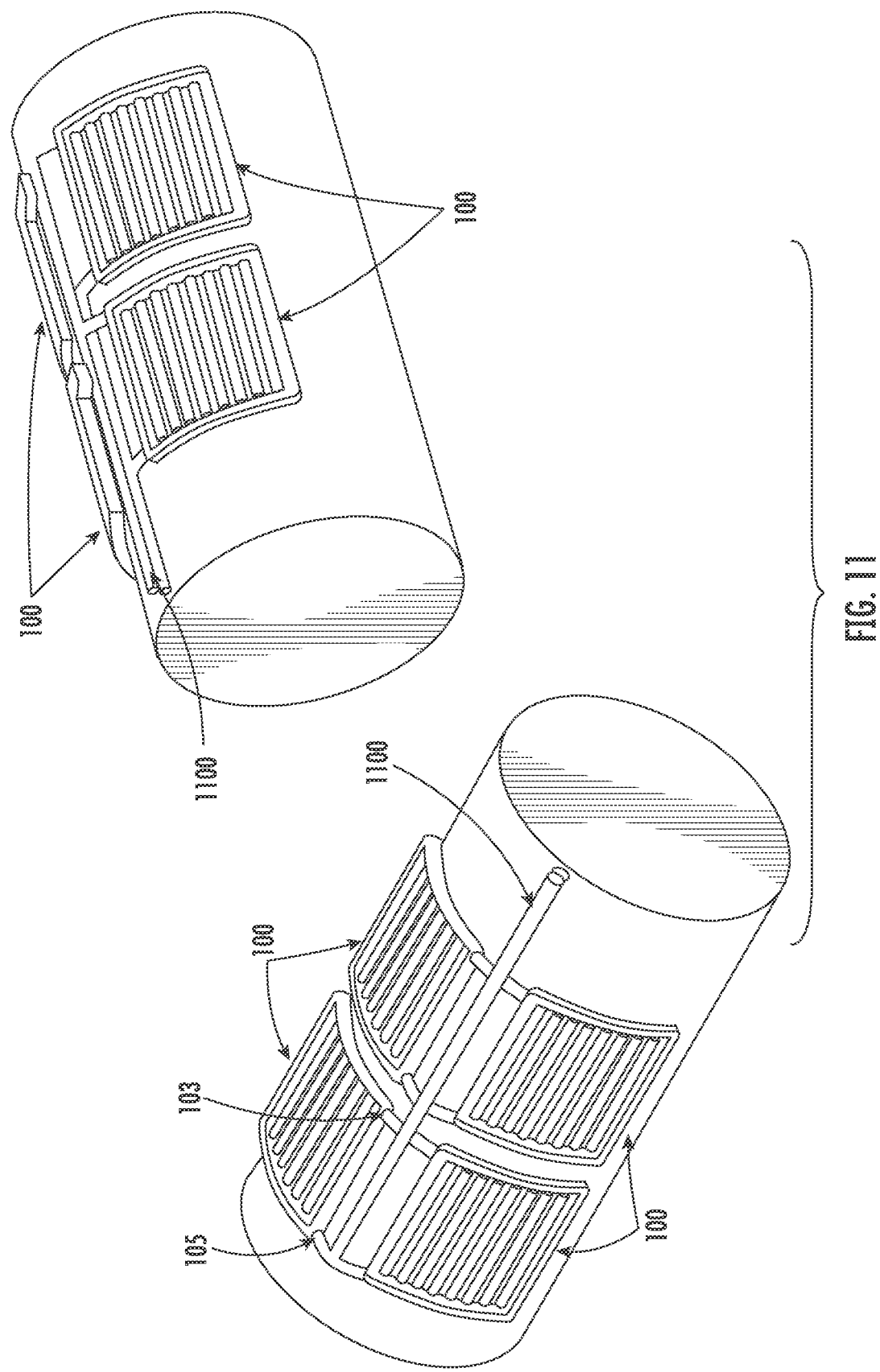

WATER PERFUSION HEAT EXCHANGE PAD FOR CONTROL OF SKIN TEMPERATURE

CROSS-REFERENCE TO RELATED APPLICATIONS

This application is a national stage application filed under 35 U.S.C. § 371 of PCT/US2018/021038 filed Mar. 6, 2018, which claims the benefit of U.S. provisional patent application No. 62/467,294, filed on Mar. 6, 2017, and entitled "WATER PERFUSION HEAT EXCHANGE PAD FOR CONTROL OF SKIN TEMPERATURE," the disclosure of which is expressly incorporated herein by reference in its entirety.

BACKGROUND

The field of thermal therapy broadly involves applying controlled temperatures to superficial tissues for enhanced healing of soft tissues or managing body core temperature to achieve perioperative normothermia or therapeutic hypothermia in response to major organ or brain ischemia. The most widely used technology for this therapy is the application of water perfused pads to the skin surface. These pads are typically fabricated from a flexible polymeric material that is formed to embody internal flow channels through which water at a specified temperature may be pumped. Conventional pads all use the same basic design, with small variations for the geometric pattern and diameter of flow channels, and the overall shape of the pads attempt to match a targeted anatomic location on the body. The pads vary greatly in size from small (e.g., a few inches square) to large enough to cover an entire limb or the torso. The pads also vary greatly in the uniformity of temperature produced on the skin surface (or in many cases, the lack thereof). This heterogeneity in performance has been measured and documented. Khoshnevis, S., Nordhauser, J. E., Cralk, N. K. and Diller, K. R., Quantitative Evaluation of the Thermal Heterogeneity on the Surface of Cryotherapy Cooling Pads, Journal of Biomechanical Engineering 136, 2014, 074503, 1-7.

In conventional water perfusion heat exchange pads, the water flow channels are quite discrete in configuration and occupy only specific areas on the pad surface. Areas of the pad between the flow channels do not receive active temperature management. As a result, the ability to manage temperature is compromised from the target value. This temperature pattern is more pronounced on some pad designs than on others. On some pads, the active temperature control area is well below 50% of the total treatment area. On the best pads, it is only about half the total treatment area.

The water flow channels function to force water to flow as homogeneously as possible over the treatment area. Without flow channels, water flow would take the path of least resistance in an open bladder configuration, and omit temperature management for a large fraction of the treatment area. Some pads divide the flow into parallel channels in an attempt to bring fresh water to as much of the treatment area as possible, but unequal flow resistance may develop because of heterogeneous pressure loading on the pad, causing differentials in local temperature management levels. Alternatively, some pads embody a serial flow pattern in which the same water reaches all areas covered by the flow channel. A major drawback of the serial flow design is that the water continuously changes temperature as it flows through the pad, resulting in uneven treatment to the tissue.

Conventional pads have water flow channels that protrude from the base material, especially when pads are filled with pressurized water, to cause flow to deliver a heating or cooling effect to a treatment site. Pads are nearly always affixed to a treatment site by straps to hold the pad in position. When a pad is strapped into position and water flow is initiated the pad will swell against the resistance of the holding straps, causing flexible flow channels to be squeezed. In some cases, the flow distribution may be altered to areas where the flow channels are not compressed, further enhancing heterogeneity of the temperature pattern produced at the treatment site.

Additionally, conventional pads consist of a single flow unit that has a fixed configuration at the time of manufacture. The entire flow configuration is sealed to prevent water leaks and cannot be modified to better suit any application need after it is fabricated. Further, conventional pads do not conform easily to the morphological contours of the body, especially when the shapes are complex and involve small radii of curvature. The result is air gaps between the pad surface and skin surface that cause large local resistances to heat transfer and uneven temperature patterns on the skin.

SUMMARY

Heat exchange pads for use on a patient are described herein. An example heat exchange pad can include a surface defining an internal volume and having a flexible patient contacting portion, an inlet fluidly connected to the internal volume for delivery of fluid into the internal volume, an outlet fluidly connected to the internal volume for removal of fluid from the internal volume, and at least one extended surface structure positioned within the internal volume to disrupt laminar flow of fluid from the inlet to the outlet. The heat exchange pad can be configured to mimic a vascular structure of glabrous skin tissue.

In some implementations, the at least one extended surface structure can be configured with a shape irregularity (e.g., a sharp turn and/or change in cross sectional diameter).

Alternatively or additionally, the at least one extended surface structure can include a plurality of fluid conduits. The fluid conduits can be configured to enhance convective heat transfer. In some implementations, at least one of the fluid conduits can have a tortuous flow path. In some implementations, at least one of the fluid conduits can have a varying inner diameter.

Alternatively or additionally, the heat exchange pad can further include a delivery header fluidly connected to the inlet and a collector header fluidly connected to the outlet. The fluid conduits can be arranged to guide fluid between the delivery and collector headers. Optionally, the fluid conduits can form parallel flow pathways between the delivery and collector headers. Optionally, the fluid conduits can coil outward from a central region of the heat exchange pad.

Alternatively or additionally, a ratio of a length to an inner diameter of at least one of the fluid conduits approximates a ratio of a length to an inner diameter of arteriovenous anastomoses (AVAs) in glabrous skin tissue.

Alternatively or additionally, a length of at least one of the fluid conduits is substantially less than a length of the heat exchange pad. Alternatively or additionally, a length of the at least one extended surface structure (e.g., the sum of the lengths of the fluid conduits connected in parallel) is substantially greater than a length of the heat exchange pad.

Alternatively or additionally, a ratio of an internal convection area to an external convention area is greater than 3:1.

Alternatively or additionally, the surface, the inlet, the outlet, and the at least one extended surface structure can be a unitary structure. For example, the surface, the inlet, the outlet, and the at least one extended surface structure can be formed or cast as a single structure. Optionally, the unitary structure can be a contiguous three-dimensional structure. In some implementations, the unitary structure can be configured to withstand greater than 2.0 atmospheres of internal pressure.

Alternatively or additionally, the flexible patient contacting portion of the surface can be configured to elastically conform to the patient's anatomy.

Alternatively or additionally, the heat exchange pad can further include a pulsating flow source fluidly connected to the inlet.

Alternatively or additionally, the heat exchange pad can further include a deformable member arranged within the internal volume. The deformable member can be configured to generate pulsatile flow.

Alternatively or additionally, the heat exchange pad can further include a fluid flowing through the internal volume. The fluid can include nanoparticles configured to enhance heat transfer.

A system of heat exchange pads is also described herein. An example heat exchange pad is described above. Optionally, the heat exchange pad described above can be modular, for example, such that a plurality of heat exchange pads are fluidly connected through the inlets and outlets thereof. By providing modular heat exchange pads, the system can be designed to the size and shape matching the personal needs of a patient.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A is an optical image illustrating the serpentine flow configuration created by welding two polymer sheets in a specific pattern. Overall dimensions are approximately 30×35 cm. Inlet and outlet are at center right. FIG. 1B is an infrared (IR) image of the surface temperatures (scale to right) when ice water is circulated through the pad. FIG. 1C is a graph illustrating heterogeneous distribution of temperatures in image pixels.

FIGS. 2A and 2B illustrate an example three-dimensional (3-D) printed biologically-inspired heat exchanger (BIHE) according to an implementation described herein. FIG. 2A is a bottom view illustrating the structure of the inlet and outlet headers and the eight pairs of delivery and collector headers. FIG. 2B is a top view illustrating thirty-three parallel curved shunt microchannels between each pair of delivery and collector headers. The curved shunt microchannels loop upwards toward the active heat transfer surface (e.g., a flexible patient contacting surface).

FIGS. 2C and 2D illustrate cross-sectional views of a heat exchange pad according to implementations described herein. FIG. 2C illustrates a cross-sectional view of a heat exchange pad on a linear contact surface. FIG. 2D illustrates a cross-sectional view of a heat exchange pad on a non-linear contact surface.

FIG. 3A illustrates a flow divider design. FIG. 3B illustrates a serpentine design. FIG. 3C illustrates a spiral trace design. FIG. 3D illustrates a vascular network design.

FIGS. 6A and 6B are IR images of BIHE prototypes perfused with heated water. FIG. 6A is an IR image of the 264 shorter curved shunt model shown in FIGS. 8A and 8B below. FIG. 6B is an IR image of the 233 longer curved shunt model shown in FIGS. 9A and 9B below. Temperature on the surface is far more uniform as shown in both FIGS. 6A and 6B as compared to a conventional heat exchanger.

FIGS. 7A and 7B illustrate a flexible BIHE mounted on a rigid 6 cm diameter cylinder. FIG. 7A shows the BIHE conformed to the curved surface geometry of the cylinder. FIG. 7B is an IR image of the BIHE perfused with 50° C. water. Surface temperature is uniform even with major bending as shown in FIG. 7B.

FIG. 8A illustrates pressure drop from inlet to outlet. FIG. 8B illustrates temperature variation across the heat transfer surface.

FIG. 9A illustrates pressure drop from inlet to outlet. FIG. 9B illustrates temperature variation across the heat transfer surface.

FIGS. 10A and 10B illustrate FEM simulation of the hydraulic and thermal function of a serpentine single channel exchanger. FIG. 10A illustrates pressure drop from inlet to outlet. FIG. 10B illustrates temperature variation across the heat transfer surface.

FIG. 11 illustrates an example system including a plurality of heat exchange pads according to implementations described herein.

FIG. 13A is a perspective view of the 3-D printed BIHE. FIG. 13B is a horizontal cross-sectional view of the 3-D printed BIHE shown in FIG. 13A. FIG. 13C is a vertical cross-sectional view of the 3-D printed BIHE shown in FIG. 13A.

DETAILED DESCRIPTION

Figure 1A:
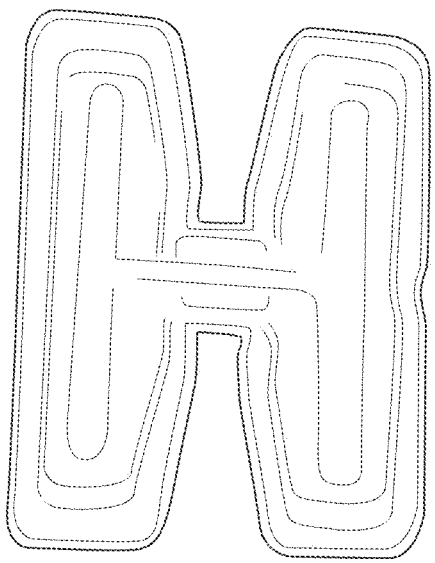
FIGS. 1A-1C illustrate thermal performance of a typical cryotherapy therapeutic pad (EBIce model 10D), i.e., a conventional serpentine flow heat exchange pad.

Unless defined otherwise, all technical and scientific terms used herein have the same meaning as commonly understood by one of ordinary skill in the art. Methods and materials similar or equivalent to those described herein can be used in the practice or testing of the present disclosure.

As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," It will be understood that the particular value forms another aspect. It will be further understood that the endpoints of each of the ranges are significant both in relation to the other endpoint, and independently of the other endpoint. While implementations will be described for water perfusion heat exchange pads for control of skin temperature, it will become evident to those skilled in the art that the implementations are not limited thereto.

In recent years, there has been an increasing awareness that heat exchange with the body surface to modulate both peripheral and core temperatures can have major therapeutic advantages. The problem is that the best performing conventional heat exchange devices, which are based on water flow through flexible polymeric pads, are unable to match the internal convective heat transport capabilities of tissue, especially on glabrous skin of a patient's palms of the hands and/or soles of the feet. Therefore, although important advances have been made medically in defining how local and core temperature manipulations can be life-saving and can also enhance the healing process for injured soft tissues, the inability to effectively implement the governing heat exchange with the patient's body is the limiting factor in realizing the medical benefits. Metal heat exchangers have also been used in conventional applications, but metal heat exchangers have their own set of drawbacks such as inflexible rigidity.

As described herein, a class of high performance, compact, biologically-inspired heat exchangers (BIHE) (sometimes referred to herein as "heat exchange pads") based on the vascular anatomy and thermal function of blood flow through the networks of arteriovenous anastomoses (AVAs) in glabrous skin have been designed, developed, and demonstrated. There is a need for medical heat transfer devices that can match the performance of glabrous skin tissue for therapeutic purposes that can be life-saving. The heat exchange pads described herein are high performance water-based heat exchangers that are sufficiently flexible to elastically conform to complex surfaces that typify anatomical shapes of the body without compromising the thermal and hydraulic efficiency. As described below, the effects on thermal and hydraulic BIHE performance of specific design features that mimic AVAs in tissue (e.g., elastic deformability; flow channel density per volume; channel diameter, length, shape, tortuosity, and spacing; and vortex generator structure geometry) have been measured. Additionally, computer simulation models of BIHEs in terms of thermal performance, internal flow pressure drop, and elastic flexibility have been developed to apply as a design tool for specific device applications. The heat exchange pads described herein can be produced using hybrid fabrication techniques based on 3-D printing and injection molding to create channel flow geometries and densities that typify the specialized vascular structure that evolved for convective heat transfer between blood and glabrous tissue.

Figure 1B:
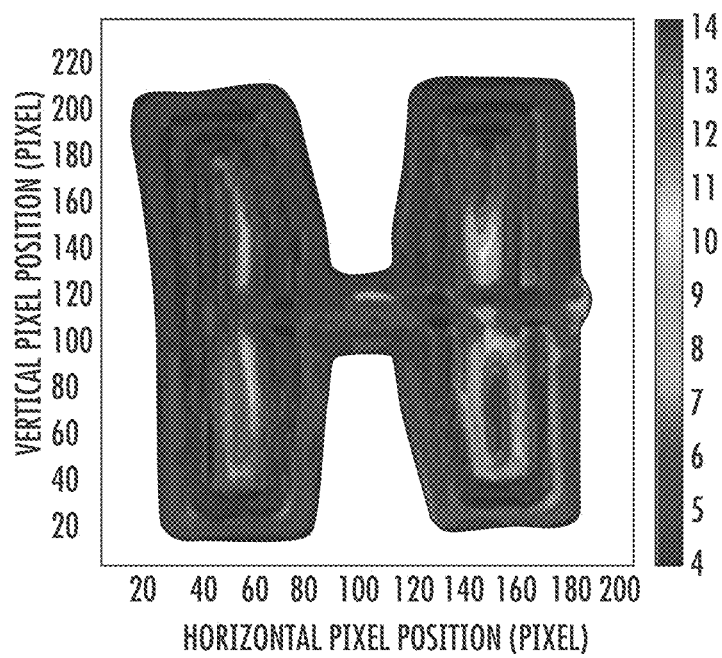
Figure 1C:
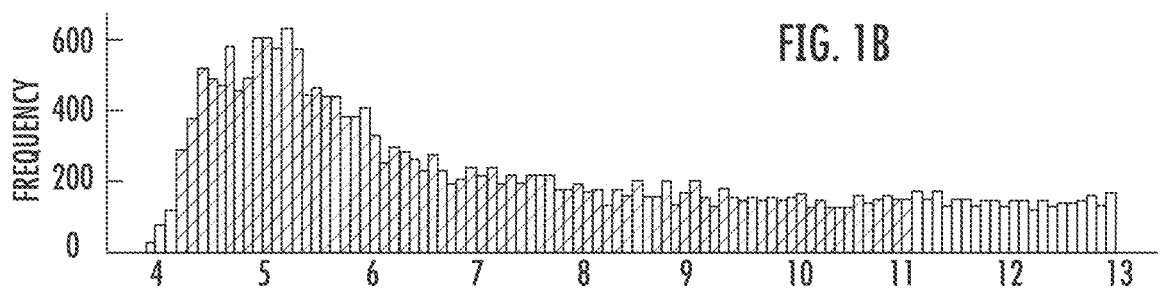
Figure 3A:
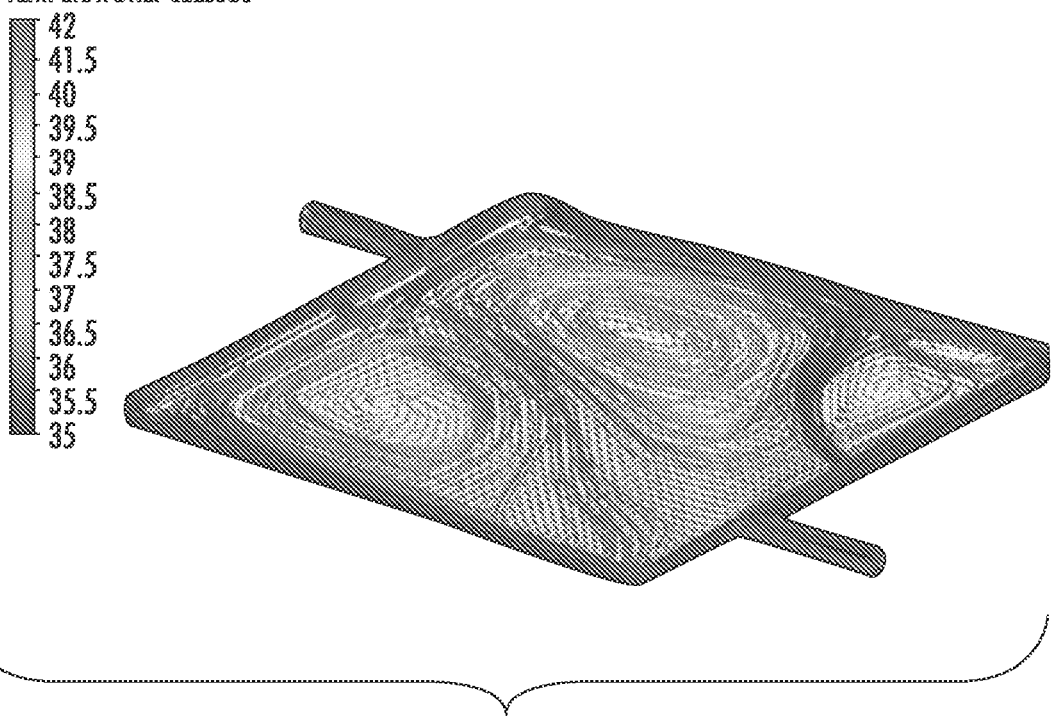
FIGS. 3A-3D illustrate FEM simulations of the thermal function of various 3-D printed BIHE designs.
Figure 3B:
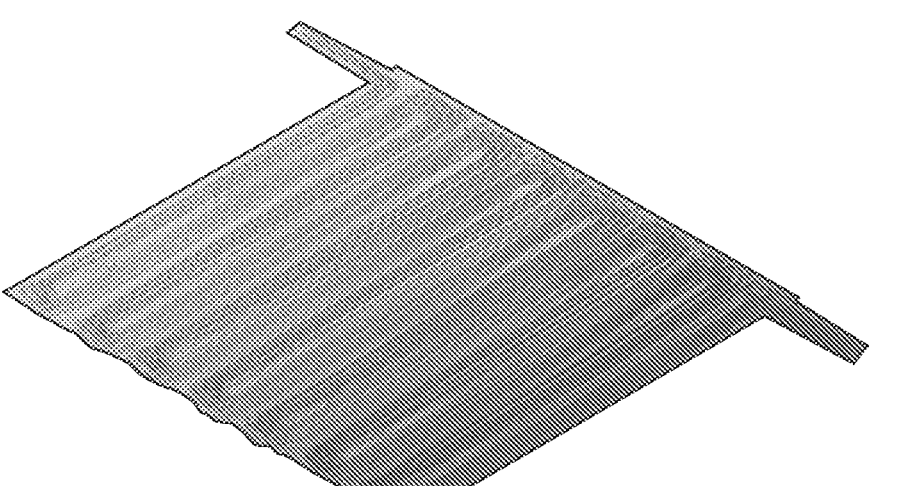
Figure 3C:
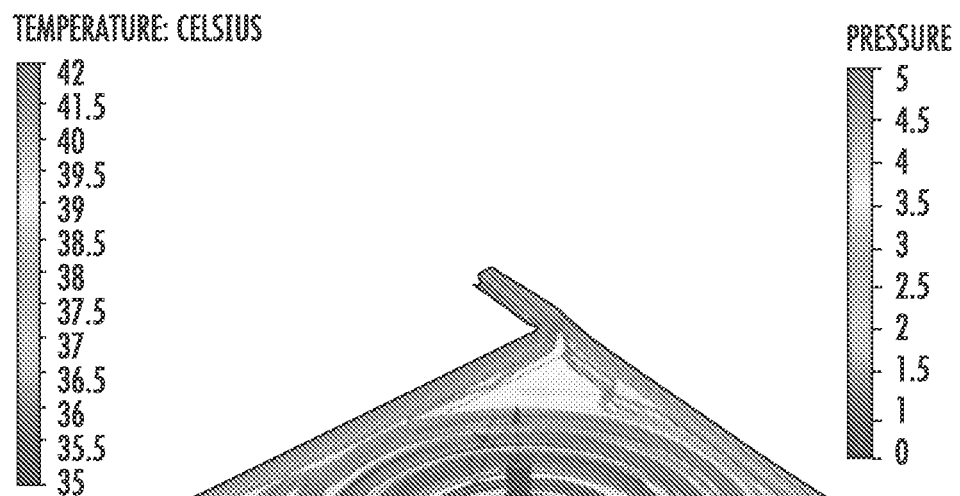
Figure 3D:
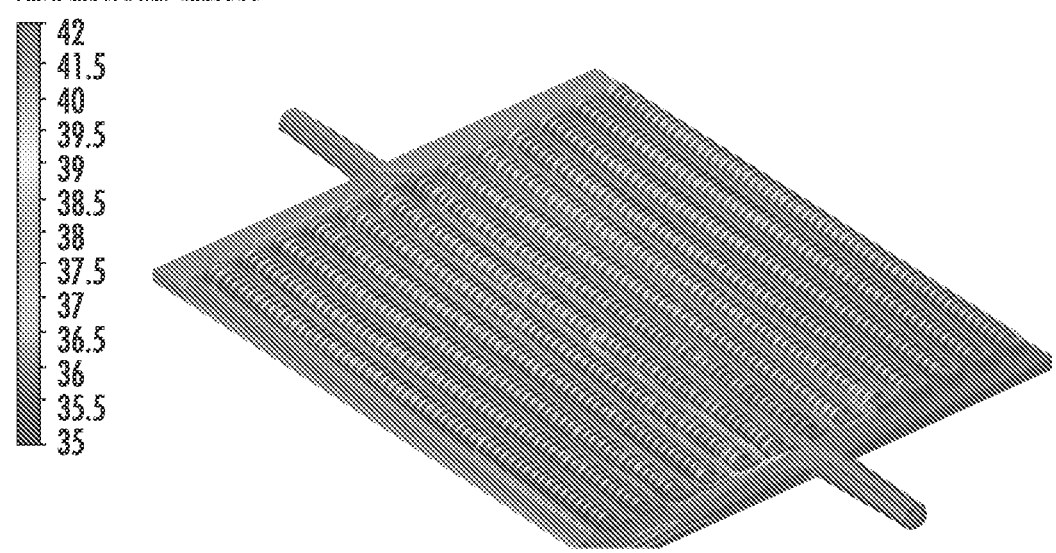

The BIHEs (or heat exchange pads) described herein can be applied for medical applications in which they can match the thermal performance of the body's built-in high capacity vascular heat exchangers in glabrous skin (e.g., particularly on the palmar and plantar surfaces of a patient). Water flow heat exchangers have been used very widely to manipulate the temperature on the skin surface for many types of thermal therapies. There are thousands of such procedures are performed on a daily basis. Dozens of conventional heat exchange pads have been evaluated. In general, the thermal boundary condition control for conventional heat exchange pads is highly heterogeneous as shown in FIGS. 1A-1C. As a group, conventional heat exchange pads such as the serpentine flow pads of FIGS. 1A-1C suffer from little or no real thermal engineering design input. They have insufficient thermal performance ($W/m^2K$) in important medical applications for glabrous skin heat transfer (GSHT). A heat transfer test rig on which the thermal and hydraulic performance of thermal therapy pads can be tested has been designed and built. The rig includes a thermal impedance well matched to that of human skin and an embedded water perfusion system that replicates convection with blood flow through glabrous skin. A wide range of conventional water flow heat exchange pads have been evaluated in more than a hundred diverse performance trials. The very best conventional heat exchange pads can produce a heat flux of about 300-400 $W/m^2K$, with most others ranging to an order of magnitude worse at about 30 $W/m^2K$. In stark contrast, the BIHE designs described herein have an order of magnitude better capability potential, e.g., in excess of 4,000 $W/m^2K$. Thus, the BIHE will have a truly disruptive effect on advancing the field of therapeutic heat transfer devices, and that will translate directly to improved health care.

Since the BIHE mimics the evolved design and performance of glabrous skin heat transfer, it is important to understand how the heat exchange vasculature internal to the skin operates and why it works so well. Convective heat transfer by blood flowing through the AVAs of glabrous skin behaves as an organic compact microchannel heat exchanger. The rate of heat transfer is a function of the vascular anatomy and blood flow conditions, including the state of vessel vasodilation. It should be understood that the body has an exquisitely elegant mechanism for regulating flow through the AVAs. The anatomy of AVAs has been studied for many decades (Grant and Bland, 1931), although the mechanisms of flow control remain an issue of physiological sophistication that is still under investigation. Regulation between full-on vasoconstriction, which results in cold hands and feet, and full-on vasodilation, which results in warm hands and feet, may occur quickly and can change the blood perfusion rate by a factor of one hundred or more (Taylor et al, 2014).

AVAs are found in glabrous (e.g., hairless) skin in areas of a patient such as the palms of the hands, soles of the feet, ears, and forehead. Their structure consists of a tight tangle of vessels positioned below the surface of the dermis (which has a thickness of about 2 mm). AVAs function as flow shunts between the arterioles and venules, allowing blood to bypass the nutritive network of capillaries. When the AVAs of two palms and two soles are vasodilated it is estimated that they can accommodate about 20% of the resting cardiac output, i.e., 1l/min (Walloe, 2016). Actual perfusion densities through AVAs have been measured to vary more than 20 fold in response to thermoregulatory state (Caldwell et al, 2014). The diameters of AVAs fall in the range between 50 and 150 µm, which is 10 to 20 times larger than capillaries. Given the inverse fourth power dependence on channel diameter of the flow resistance of a fluid moving through a tube, vasodilated AVAs provide a high throughput pathway for blood as it moves through the peripheral circulation and returns to the heart. The density of anastomoses per unit surface area falls in the range 50-500/cm$^2$, which is an order of magnitude larger than for capillaries (Walloe, 2016; Taylor et al, 2014). The length of an AVA can be as large as 2-4 mm, although most are considerably shorter (Molyneux and Bryden, 1981). Most AVAs have a highly tortuous shape that contributes to the effectiveness for convection heat transfer.

Various heat fluxes have been measured on the surface of glabrous skin as a function of the environmental fluid (air or water) and the applied temperature difference. As anticipated, smaller fluxes were achieved in air and larger in water. In either case, the heat fluxes are smaller than has been measured with microchannel heat exchangers while extracting heat from solid state electronic devices for two reasons. One is that the applied temperature differences must be much smaller to avoid limiting physiological factors. The temperature of blood flowing through AVAs normally will be on the order of 36° C. The upper source limit for heating is about 43° C., above which it is possible to cause thermal injury to tissue (Diller, 1992). The lower source limit for cooling is about 20° C., below which locally induced vasoconstriction occurs, obviating the ability for convection heat transfer. Heller and Grahn (2012) measured heat fluxes on the palm of hyperthermia subjects exposed to a pad with water circulating at 16° C. For a total blood to water temperature difference of about 20° C., the flux was 0.17 W/cm$^2$ at atmospheric pressure, and 0.23 W/cm$^2$ when a negative pressure of 40 mmHg was applied to distend the AVAs to increase blood flow. Cooling experiments have been conducted via glabrous skin heat transfer with equivalent thermal performance, but with conventional water perfused heat exchanger pads having limited performance capabilities. Net heat flows were on the order of 200 W in comparison with a basal metabolic rate of about 80 W.

Microchannel heat exchangers offer numerous advantages over conventional macroscopic alternatives, including a high level of heat transfer per unit device volume coupled with small size and weight, and have accordingly been the topic of intense, high level research over the past several decades (Kandlikar et al, 2013). Electronics cooling has been a major motivator for the development of this technology as the power density of silicon devices has increased continuously. Small dimensioned flow channels inherently embody a large surface to volume ratio, leading to the desired outcome of increased heat transfer rates (Kandlikar, 2012). The tradeoff of small flow channels is an increased resistance to flow. Technologies such as electro-osmotic flow (Al-Rjoub et al, 2015) have been developed to enhance the flow through microchannels, although application to medical devices could be challenging.

Many of the properties of microchannel heat exchangers are complementary to the features of blood flowing though AVAs (Hassanipour and Lage, 2010). These include a high density of small flow channels. The primary application of microchannel heat exchangers in the medical field has been limited to the cooling of remote instrumentation components, with no translation and adaptation for heat transfer directly to patient tissue. Thus, there is both a need and a prospect to develop new microscale heat exchanger capabilities so that they may be used for medical purposes directly on the surface of the human body. Nearly all existing microchannel heat exchangers are rigid, and rigidity poses compromises for interfacing with the body surface. Overcoming the rigid character of microchannel heat exchangers is not identified as a desired contribution to the field in the context of the traditional applications of these devices (Ohadi et al, 2013).

As described herein, the BIHEs (or heat exchange pads) are configured to mimic the governing features of GSHT via blood flow through AVAs. The BIHEs described herein are needed to be able to equal the GSHT efficacy to accomplish critical therapeutic processes. No conventional heat exchangers satisfy this requirement. Key features of GSHT have been designed into the BIHEs described herein, resulting in heat exchange pads having unique assets and capabilities. Features of the BIHEs described herein include, but are not limited to:

The ability to flexibly and reversibly deform macroscopically, such as to conform to a patient's body contours and to accommodate distortion when a joint bends, without compromising the thermal and hydraulic performance of the operating fluid (blood in the AVAs, water in the BIHE);

A highly dense network of flow conduits having tortuous shapes that enhance convective heat exchange with the working fluid;

Flow of the operating fluid distributed among a very large number of parallel flow pathways (e.g., fluid conduits) resulting in minimal viscous resistance per total volume flow rate;

Lengths of individual fluid conduits that are substantially less than the overall dimensions of the BIHE, affording enhanced net heat transfer;

Efficient multi-tiered distributing and collecting manifold header systems (e.g., delivery and collector headers) that connect with a large network (hundreds) of individual heat exchange channels (e.g., fluid conduits);

A large ratio of convective heat exchange surface area to total BIHE volume that is typical of microchannel heat exchangers;

A large ratio of internal convective heat exchange surface to the BIHE external surface across which transport occurs with the environment;

Pulsatile flow to enhance mixing and convective efficiency of the operating fluid as it passes through the fluid conduit network of the BIHE;

A BIHE body with a low resistance to bending and with an internal structure that supports microchannels (e.g., fluid conduits and/or headers) against collapsing during deformation;

Uniform distribution of flow through a network of hundreds of parallel microchannels (e.g., fluid conduits and/or headers);

Scalability from small individual modules to large device dimensions that incorporate multiple modules via branching header systems;

Versatile fabrication technologies based on additive 3-D printing combined with hybrid molding methods that enable building complex internal structures into the flow channels that are impossible to replicate using subtractive manufacturing procedures and that enhance convective exchange efficiency;

A high thermal conductivity flexible polymer BIHE body created by doping with custom graphite powder;

BIHE design based on modular construction that can be customized easily to conform to the local morphology of a treatment site;

BIHE design offering low flow resistance and high water flow rates for high rates of heat transfer between circulating water and skin on which the BIHE is placed;

The modularity of the heat exchange surfaces enable the size and shape to be altered to match the personal needs of a patient;

Since the conformability of the BIHE is very good, air gaps between the BIHE and skin surface are minimized or eliminated, providing a more uniform temperature application onto the treatment surface;

BIHE can be provided with an adhesive coating to produce good thermal contact with the skin surface to promote effective heat transfer;

BIHE can be formed easily from modular components by the health care provider from a small number of module shapes, enabling a large range of devices to be provided from a minimum component inventory (e.g., similar to forming a 3-D LEGO structure);

Water is fed to and collected from individual modules via a specially designed plenum header;

Barbed or clipped connections can be used between modules and the plenum header and among multiple modules;

Water can be delivered and collected in a plenum header that is shaped to ensure a uniform flow velocity as water is bled off to supply local modules (e.g., similar to air conditioning distribution ducts that become smaller further from the source);

The flow passageways for water are supported in a pad matrix so that the passageways are resistant to deformation when the BIHE is applied to the skin and when it is flexed to conform to the skin shape;

BIHE matrix can be biomaterial with the outer surface insulating against the environment and the inner surface highly conductive to enable uniform distribution of temperature over the treatment site such that the conductive surface acts to spread the temperature and reduce gradients on the treatment site;

Straps can be used to further stabilize BIHE attachment to the treatment site; and/or BIHE design can provide a simple and inexpensive approach to guard against water leaks.

Referring now to FIGS. 2A and 2B, an example 3-D printed BIHE as described herein is shown. It should be understood that a BIHE is also sometimes referred to herein as a "heat exchange pad." An example heat exchange pad 100 can include a surface defining an internal volume 101 and having a flexible patient contacting portion, an inlet 103 fluidly connected to the internal volume 101 for delivery of fluid into the internal volume 101, an outlet 105 fluidly connected to the internal volume 101 for removal of fluid from the internal volume 101, and at least one extended surface structure 110 positioned within the internal volume 101 to disrupt laminar flow of fluid from the inlet 103 to the outlet 105. The heat exchange pad 100 can be configured to mimic a vascular structure of glabrous skin tissue. In some implementations, the at least one extended surface structure 110 can be configured with a shape irregularity (e.g., a sharp turn and/or change in cross sectional diameter as described below).

Referring now to FIGS. 2C and 2D, cross-sectional views of a heat exchange pad 100 are shown. The surface 102 defining the internal volume is shown in FIGS. 2C and 2D. A cross sectional view 110A of the extended surface structure is also shown in FIGS. 2C and 2D. The surface 102 has a flexible patient contacting portion. In FIG. 2C, the heat exchange pad 100 is on a linear contact surface. In FIG. 2D, the heat exchange pad 100 is on a non-linear contact surface.

Referring again to FIGS. 2A and 2B, the at least one extended surface structure 110 can include a plurality of fluid conduits. As shown in FIGS. 2A and 2B, the fluid conduits can be arranged to guide fluid between a delivery header 120 and a collector header 130. In FIGS. 2A and 2B, there are eight rows of fluid conduits arranged in parallel, where each row includes thirty three fluid conduits guiding fluid between respective delivery and collector headers. It should be understood that the number of rows and/or fluid conduits in FIGS. 2A and 2B are provided only as examples. In other words, a heat exchange pad can have more or less rows and/or fluid conduits in accordance with the disclosure provided herein. The fluid conduits can be configured to enhance convective heat transfer. In some implementations, at least one of the fluid conduits can optionally have a tortuous flow path. In some implementations, at least one of the fluid conduits can optionally have a varying inner diameter. Example fluid conduits having shape irregularities are described herein. This disclosure contemplates that such fluid conduits can mimic the vascular structure of glabrous skin tissue. As described above, the heat exchange pad 100 can include the delivery header 120, which is fluidly connected to the inlet 103. The heat exchange pad 100 can also include the collector header 130, which is fluidly connected to the outlet 105. Optionally, the fluid conduits can form parallel flow pathways between the delivery and collector headers 120 and 130 as shown in FIGS. 2A and 2B.

As described below, the heat exchange pad 100 can be a unitary structure. For example, the surface, the inlet 103, the outlet 105, and the at least one extended surface structure 110 can be a unitary structure. In some implementations, the surface, the inlet 103, the outlet 105, and the at least one extended surface structure 110 can be formed or cast as a single structure. This disclosure contemplates that this construction is in contrast to forming the heat exchange pad 100 from a plurality of welded polymeric sheets. Optionally, the unitary structure can be a contiguous three-dimensional (3-D) structure, for example, the heat exchange pad 100 can be printed using a 3-D printer. Alternatively or additionally, the heat exchange pad 100 can be used in a system of heat exchange pads as described below. In other words, the heat exchange pad 100 can be modular such that the heat exchange pad 100 can be connected with other heat exchange pads. For example, with reference to FIG. 11, a plurality of heat exchange pads 100 can be connected together in a system. The heat exchange pads 100 can be fluidly connected via a conduit system 1100 through the inlets and outlets of the heat exchange pads 100. In FIG. 11, an inlet 103 and an outlet 105 of one of the heat exchange pads is labeled for reference. By providing modular heat exchange pads, the system can be designed to the size and shape matching the personal needs of a patient.

The heat exchange pad 100 can mimic the vascular structure of glabrous skin that provides the primary site of high efficiency heat transfer to and from the body surface in virtually all mammalian and avian species. The vascular structure in glabrous skin is characterized by shape irregularities including sharp turns and changes in flow cross section. Although the glabrous vessels and blood flow velocities indicate that the flow be largely laminar, the tortuous and complex structure of the vessels may provide significant flow disruption to enhance the heat transfer to be more efficient that would occur for a classical undisturbed laminar flow. Elements in either geometry or time (pulsations) can disturb laminar flows, thereby increasing the efficiency of convective heat transfer. The conditions for maintaining laminar flow generally require a very simple geometry, such as a long straight tube, and steady flow. Geometrically complex and irregular shapes interior to a flow channel can cause the flow to become unstable and even become locally turbulent, which would increase convective heat transfer efficiency. Further, physiological blood flow is strongly nonsteady, having a pulsatile nature. This unsteady flow causes disruptions in laminar flow. Thus, the heat exchange pad 100 can include fluid conduits having shape irregularities and/or a source of pulsatile flow. Also, the presence of blood cells in blood makes maintenance of laminar flow more difficult, creating a more chaotic flow pattern. The BIHEs described herein can incorporate these features.

Figure 12:
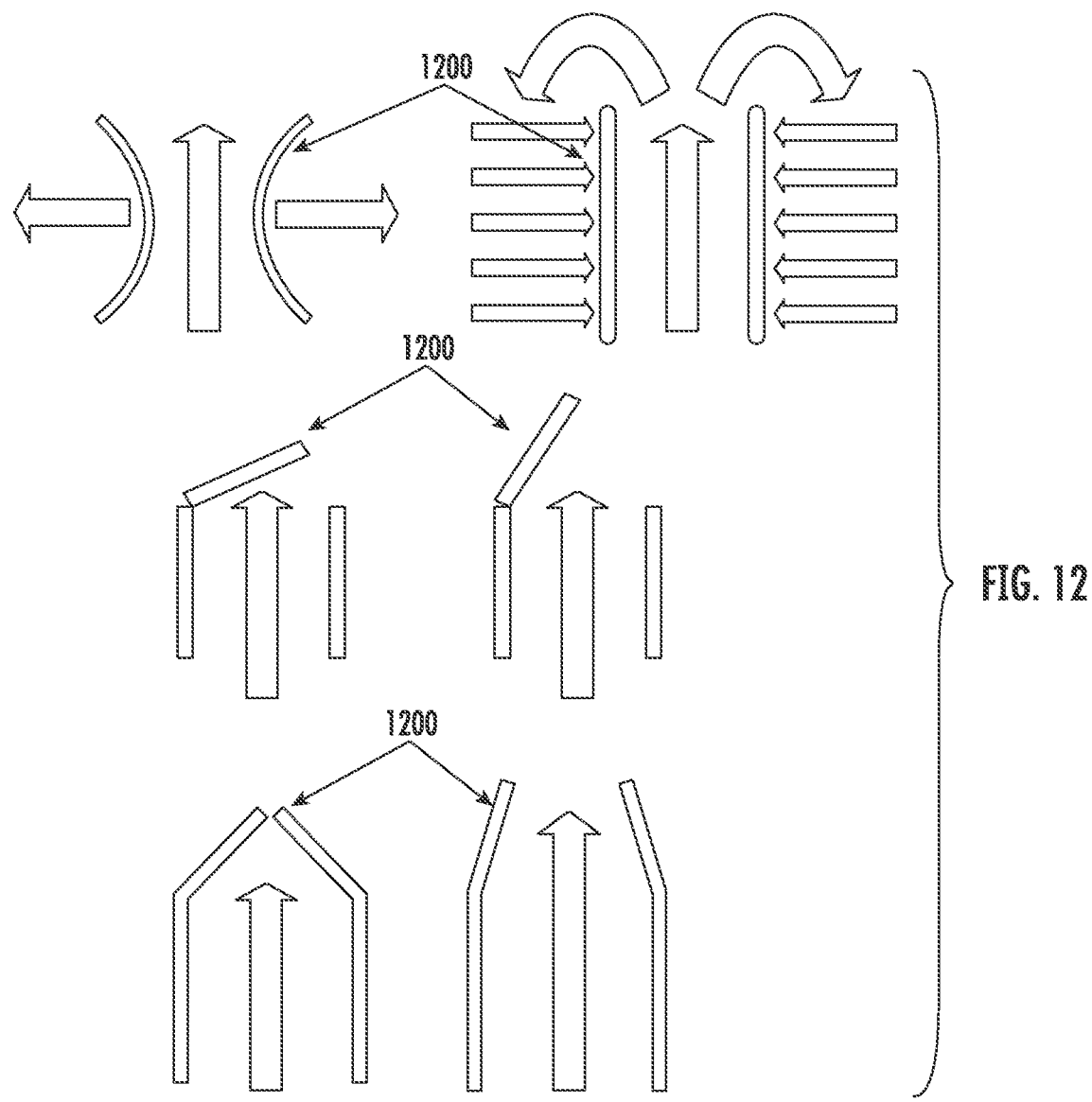
FIG. 12 illustrates example deformable members that can be arranged within an internal volume of a heat exchange pad according to implementations described herein.

The heat exchange pad 100 can incorporate one or more structural properties of the vascular network found in glabrous skin. These include: flow being guided in discretely defined geometric channels (e.g., fluid conduits); structural elements designed to disrupt laminar flow patterns to create chaotic enhancement of convection effects; internal extended surfaces to improve the heat transfer surface area to volume ratio; a high density of flow channels (e.g., fluid conduits) per unit heat transfer surface area; internal structures that may deform elastically to periodically disrupt the flow pattern into pulsations that cause breakdown of laminar structure; and flow through a large number of small bore parallel pathways (e.g., fluid conduits) connected to flow efficient inlet and outlet headers. Example elastically deformable internal structures (e.g., deformable members) that can be arranged within an internal volume of a heat exchange pad (e.g., internal volume 101 of FIGS. 2A and 2B) are shown in FIG. 12. For example, deformable members 1200 can be arranged in within the internal volume and can disrupt the flow pattern and/or generate pulsatile flow. The flow pattern and deformation are shown by arrows in FIG. 12. The heat exchange pad 100 can also be coupled to a pulsating flow source to provide further internal mixing effects.

In addition, introduction of foreign particles into the flowing fluid (e.g., water for the intended medical applications) can induce disruptions in laminar flow that can enhance convection. In blood these particles are cells. In the heat exchange pad 100, the particle inclusions may be nanoparticles with special heat transfer enhancement properties. In other words, the heat exchange pad 100 can include a fluid having nanoparticles configured to enhance heat transfer. The heat exchange pad 100 can be used in conjunction with a thermoelectric temperature control source that does not rely on melting ice to provide the base cooling function. Melting ice would dilute the concentration of circulating nano particles unless they were included in the water when it was frozen. This requirement is impractical for many applications such as home use where it would be difficult/confusing to freeze nano particle-laced water.

BIHEs including microchannel heat exchangers (e.g., fluid conduits and/or headers) that mimic the vascular structure found in glabrous skin, accommodating competing thermal, hydraulic, and elastic requirements have been designed and fabricated. BIHEs can provide greater efficacy for many medical applications of thermal therapies than has been possible heretofore. Structural and fabrication principles of BIHE can be translated to other uses. As described herein, a number of microchannel alpha prototype configurations have been fabricated. It should be understood that the BIHEs described herein are provided only as examples. This disclosure contemplates that BIHEs having other designs can be fabricated according to this disclosure. A variety of different alpha prototypes have been designed, built, and tested in various formats. These prototypes serve as platforms to devise fabrication methods for creating tortuous interior micro flow channels. Mimicry of the vascular structure of glabrous skin is achieved by using 3-D printing methods. The structural complexity that can be built into the flow channel configurations is limited by the resolution of the 3-D printers.

Referring again to FIGS. 2A and 2B, a BIHE fabricated of clear photopolymer on a Formlabs 3-D printer is shown. The BIHE (e.g., heat exchange pad 100) includes a 3 mm diameter inlet header (e.g., inlet 103) and a 3 mm diameter outlet header (e.g., outlet 105), eight parallel 2 mm diameter×5 cm long straight delivery and collector headers (e.g., delivery and collector headers 120 and 130) that mimic arterioles and venules, and 33 parallel 1 mm diameter×10 mm long curved shunts (e.g., extended surface structure 110) that mimic AVAs. The curved shunts in FIGS. 2A and 2B are the fluid conduits that guide fluid between the delivery and collector headers 120 and 130 as described herein. Optionally, a ratio of a length to an inner diameter of at least one of the fluid conduits approximates a ratio of a length to an inner diameter of AVAs in glabrous skin tissue. For example, in FIGS. 2A and 2B, the ratio of length to diameter of a curved shunt is about 10:1, which approximates that of AVAs. It should be understood that the 10:1 ratio is provided only as an example. This disclosure contemplates that a ratio of the length to the inner diameter of an extended surface structure can have a value more or less than 10:1. In FIGS. 2A and 2B, the outer dimensions of the heat exchange pad 100 are 59 mm×54 mm×5 mm. Optionally, a length of at least one of the fluid conduits is substantially less than a length of the heat exchange pad 100. For example, in FIGS. 2A and 2B, each curved shunt is about 10 mm as compared to the 59 mm length of the heat exchange pad 100. Thus, the ratio of the length of the heat exchange pad to the length of a fluid conduit is about 6:1 in FIGS. 2A and 2B. This disclosure contemplates that a ratio of the length of the heat exchange pad to the length of a fluid conduit can have a value more or less than 6:1, which is provided as an example. Additionally, the fluid conduits are connected in parallel to form the extended surface structure 110. For example, in FIGS. 2A and 2B, 33 curved shunts are connected in parallel to form the extended surface structure. The length of an extended surface structure (e.g., the sum of the lengths of the fluid conduits connected in parallel) can be substantially greater than the length of the heat exchange pad $$\left(\text{i.e., } \frac{\text{length of heat exchange pad}}{\text{length of extended surface structure}}\right).$$

For example, in FIGS. 2A and 2B, the length of the extended surface structure 110 is about 330 mm (i.e., 33×10 mm), which is substantially greater than the length of the heat exchange pad 100 itself (e.g., 59 mm in FIGS. 2A and 2B). This disclosure also contemplates that this ratio can be a tuning parameter for thermal performance. The total number of shunts (microchannels or fluid conduits) is 264 in FIGS. 2A and 2B. The extended surface structure 110 described above, which includes a plurality of fluid conduits in parallel, results in a significantly larger net internal length of convective heat transfer surface as compared to the outside dimension of the heat exchange pad. In other words, the ratio of the internal convective surface area to the volume of the heat exchange pad is a large number. This design mimics the ratio of AVA surface area to the volume of glabrous skin in which the AVA are embedded. Alternatively or additionally, a ratio of an internal convection area to an external convention area can optionally be large. For example, in FIGS. 2A and 2B, the ratio of internal convection area to external conduction area is more than 3:1. It should be understood that the 3:1 ratio is provided only as an example. This disclosure contemplates that a ratio of internal convection area to external convention area can have a value more or less than 3:1. It should be understood that this ratio is often less than 1:1 in conventional heat exchange pads. It should also be understood that the BIHE design (including, but not limited to the number and/or arrangement and/or dimensions of headers and fluid conduits) in FIGS. 2A and 2B are provided only as examples. This disclosure contemplates that alternate structures are possible, for example, as shown in FIGS. 3A-3D, 5, 9A and 9B, and 10A and 10B.

A fabrication method has been developed to create a polymer BIHE such as the heat exchange pad shown in FIGS. 2A and 2B with a high level of flexibility and with shapes that cannot be produced by traditional micromachining methods. One example method uses a multi step process as follows. First, an internal flow network is designed in a 3-D CAD program and transferred to a 3-D printer where it is produced in rigid polylactic acid (PLA). Next, the silicone polymer body of the BIHE is molded around the PLA and cured. The PLA is structurally rigid and maintains the integrity of the internal flow network during the molding process. Finally, the PLA is dissolved out the of silicone body with sodium hydroxide. Owing to the small dimensions of the microchannels, it is difficult for the dissolved PLA to passively diffuse from the silicone body. Therefore, the PLA removal process is enhanced with a pulsatile infusion pump and ultrasonic vibration that produce a clean BIHE. Various options are available for the dissolvable printed channel structure and its solvent combination as well as for the flexible polymer. For example, printed structure candidate materials and solvents include: PLA and sodium hydroxide; PVA and warm water; HIPS and D-limonene. Candidate casting and injectable polymers for the pad body include: silicone with varying durometer polyurethane rubber; COOLPOLY E8101, E8102, E8103, E8104 Thermally Conductive Thermoplastic Elastomer (TPE); and many photocured polymers that can be printed via SLA. This disclosure contemplates that casting and injection molding can also be used for fabricating the BIHE body.

The 3-D printing methods used to create the flow pathway and convective interface for the fluid perfused through the BIHE provide many diverse structural design options. The shapes of the headers and microchannels that can be created are boundless, as are choices for heat transfer enhancing structures such as internal fins, vortex generators, and prescribed surface roughness (Kandlikar et al, 2014). The material of which the BIHE body is fabricated can be selected to achieve any desired set of performance characteristics. Example critical material properties are the thermal conductivity and the elastic bending flexibility. Various polymers provide an acceptable level of flexibility in terms of their Young's modulus, with a relatively low level of stress necessary to produce a substantial deformation. The range of Young's moduli for polymers is quite broad, ranging from about 0.001 to 1 GPa. For comparison, the Young's modulus for human skin in vivo is about 0.01 MPa (Agache et al, 1980; Pailler-Mattel et al, 2008), making it considerably more susceptible to defamation. A related property is the hardness of the BIHE in comparison to skin. The shore hardness durometer value for normal skin is in the range of 30 (Falanga et al, 1993), whereas silicone polymers cover a wide range, but many are in the range of skin. In addition to the modulus of elasticity of the BIHE body, the resistance to bending is also dependent on the moment of inertia about the neutral axis. The moment of inertia is a direct function of the internal geometry and its orientation to the axis of bending. The BIHE has a much larger resistance to the collapse of internal flow channels (e.g., flow conduits and/or headers) during bending than does a conventional serpentine geometry heat exchanger as shown in FIGS. 1A-1C. Collapsed channels will cause starvation of the flow and compromise of hydraulic performance. One of the performance properties that is measured is the alteration in the internal flow resistance as the exchanger body is subjected to progressive bending. Initial qualitative testing has demonstrated that the BIHE is much more resistant to channel collapse than is a larger diameter serpentine exchanger channel (e.g., the serpentine flow heat exchange pad shown in FIGS. 1A-1C).

Another important property of a heat exchange pad is the thermal conductivity, which is particularly challenging when a polymer material is used to obtain flexibility owing to the low native conductivity. Initial simulations have demonstrated a strong correlation between the material thermal conductivity and the rate at which heat can be transmitted between an internal flowing fluid and the environment. GRAFTECH INTERNATIONAL HOLDINGS INC. ("GrafTech") of Parma, Ohio manufactures carbon products with superior thermal properties that can be used for the BIHEs described herein. GrafTech GP44-R graphite powder may be used to dope the polymer raw material prior to fabrication to increase the thermal conductivity. Formation of a graphite polymer composite is an established method to significantly increase thermal conductivity while retaining flexible mechanical properties (Sengupta et al, 2011; Wang et al, 2011). It is possible to manipulate the thermal conductivity of a polymer matrix across a range from 0.15 to 10 W/mK by increasing the concentration of graphite up to 10 wt. %. Graphite is highly anisotropic as a consequence of it structure that consists of broad, thin plates having very high in-plane conductivity of 3,000 W/mK, with a cross plane value of 6 W/mK (Yu et al, 2008). The plate planar dimension can be 50 μm, so orientation with respect to the vector between the convection loops and the active heat transfer surface of the BIHE is important. The 3-D printing process for fabrication affords the opportunity to design the internal structure of the BIHE very carefully, including such features as the thickness of the body material between the convection loops and the heat exchange surface to balance the tradeoff between minimizing thermal impedance and rupture resistant rupture (as a function of internal water pressure). A thickness of 500 μm has been used for the prototypes described herein. Doping the polymer with graphite power will also change the elastic and hardness properties. The natural lubricity of graphite can aid in the flexibility of the doped polymer, and its inertness benefits applications in medical devices such as the BIHE.

The BIHEs described herein can be fabricated as a single body (e.g., sometimes referred to herein as a "unitary structure") with no seams. This unitary structure provides a superior and unique control over the geometry and density of the flow passageways of water through the exchanger, and also enables much more robust mechanical properties. This is in contrast to conventional water flow medical heat exchangers that consist of multiple polymer sheets that are welded together, for example, around their perimeter and often with patterns of interior welds as spots or lines to direct the interior flow of circulating water. Conventional heat exchange pads made of multiple polymer sheets are structurally weaker, much more prone to developing leaks under internal pressure, and incapable of maintaining their internal flow integrity with subjected to external loading. Welded polymer sheet heat exchangers typically are able to withstand about 1.5 atmospheres (21 psi) of pressure from circulating water before the risk of bursting to form a leak. The BIHE described herein can withstand a two fold greater internal pressure. For example, the BIHE can be designed to withstand greater than 2.0 atmospheres of internal pressure. It should be understood that 2.0 atmospheres is provided only as an example. This disclosure contemplates that the BIHE can be designed to withstand more or less than 2.0 atmospheres. This pressure level is at the limit of other flow system components such as tubing connectors, so it is practically the highest pressure for which a heat exchanger system need be designed. The higher pressures available in the BIHE provide the ability to create a higher flow rate of water within the exchanger that results in greater convective heat transfer efficiency than is possible in traditional welded plastic sheet exchangers.

Some conventional pads operate under negative pressure flow in order to reduce leak susceptibility. Further, since the BIHE has a contiguous three-dimensional structure rather than just a network of spot and line welds, as do conventional heat exchange pads, the BIHE has a much more substantial internal structural integrity and is able to resist collapse of flow channels (e.g., fluid conduits and/or headers) as macroscopic bending is applied to the device to conform it to an anatomical shape. It is not unusual for conventional welded sheet heat exchange pads to become starved for internal convective flow in areas where there is deformation with a small radius of curvature. In a contrasting sense, another drawback of conventional welded sheet heat exchange pads is that they swell when pressurized with internally flowing water, taking on a more rounded geometry and loosing contact area with the surface to which they are applied, degrading their heat transfer efficacy. Also, a localized surface pressure is applied to the skin that can reduce blood flow in the tissue at the site of application and compromise internal heat transfer. In comparison to structures formed by welding along a line or at a point, the BIHE internal unitized structure provides distributed support against opposing sides of the exchanger moving apart and deforming went the circulating water pressure increases, avoiding loss of contact area with the skin and heat transfer as well as leak resistance. The BIHEs described herein have very minimal swelling when internally pressurized and maintain internal flow when subjected to bending as shown in FIGS. 7A and 7B below.

The BIHEs described herein can be fabricated from a broad range of materials and designed with properties to enhance the mechanical and thermal properties, in comparison to plastic sheets used for conventional heat exchangers. Heat exchangers formed by welding standard plastic sheets together along their perimeter and interior within the body to form flow channels, provide very limited flexibility or options for optimizing or improving mechanical and thermal performance.

A flexible header system can be developed to connect a plurality BIHEs for scaling to cover areas larger that for an individual BIHE. In other words, the BIHEs described herein are modular in design and can be interconnected with other BIHEs. This approach is equivalent to the vascular network in glabrous skin in which many branched AVA complexes are connected to supply arteries (arterials) and collector veins (venules). The header connections can be positioned distally to a grouping of BIHE positioned proximally to a target heat transfer surface. The header connections can contribute to inter-BIHE flexibility to complement the elastic intra-BIHE flexibility.

The benchmark for medical heat transfer on the skin surface is a water perfusion pad fabricated from welded polymer sheets with a serpentine or bladder macroscopic flow pattern. As described above, a conventional serpentine flow heat exchange pad is shown in FIGS. 1A-1C. Many styles exist, nearly all of which have been evaluated quantitatively. The BIHE $W/cm^2K$ and pressure drop for a standard water flow through rate can be compared with conventional heat exchange pads as described below.

Models of the internal flow structure around which a polymeric heat exchanger body can be cast have been 3-D printed. Dissolving a water soluble interior mold from a microchannel network has been addressed as described herein. For example, it is possible to dissolve the interior mold by heating the system in an ultrasound bath during dissolution. Although obtaining an even distribution of water flow among a large number of parallel microchannels (e.g., fluid conduits and/or headers) can be difficult, the data shown in FIG. 5 indicates progress has been achieved. Computer fluid dynamics (CFD) modeling can be applied as a design tool to shape the geometry of header from which the parallel microchannels branch to produce uniform flows in the channels. There are many options for header geometries that can be interrogated numerically for optimization. A BIHE can be created that is sufficiently flexible to conform to body anatomies without deforming the interior flow channels to significantly increase the flow resistance. Vascular flow mimicry network geometries are far more resistant to collapse upon bending that are macroscopic channels, especially when deformed normal to the channel axis. Finite element modeling (FEM) elastic analysis is a primary tool for this purpose that has been implemented. A well dispersed distribution of graphite powder oriented within the polymer body structure can be achieved to provide highest thermal conductivity enhancement.

Figure 4:
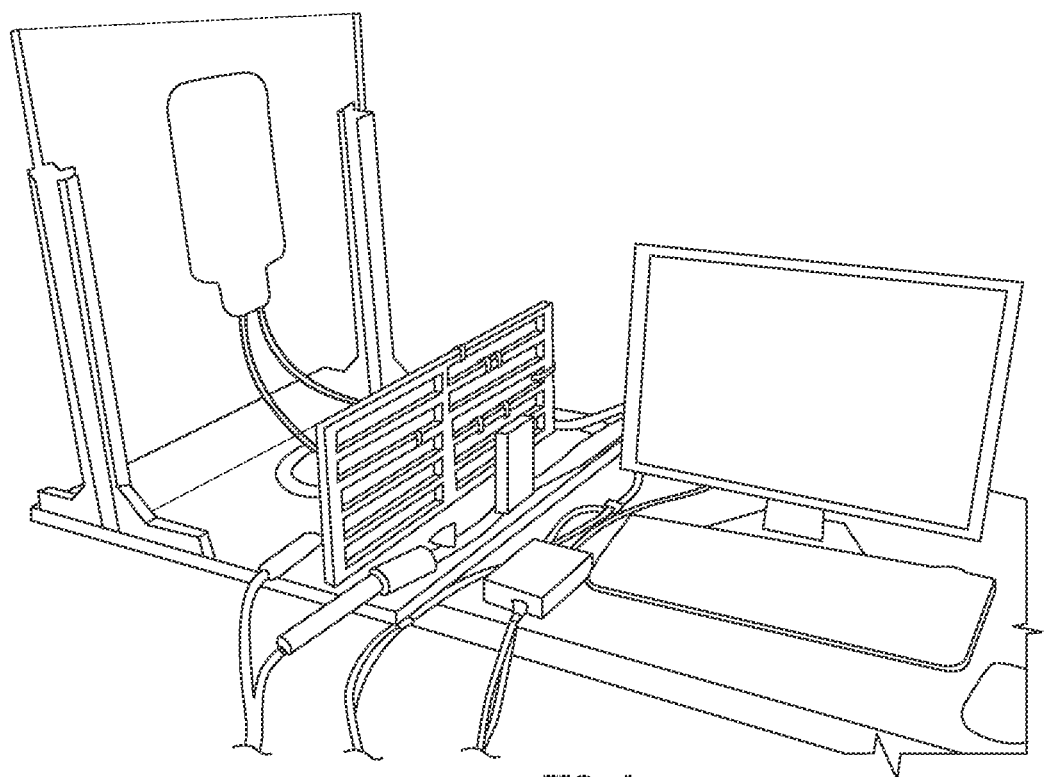
FIG. 4 illustrates a test rig for evaluating heat transfer and fluid flow functions of water perfusion pads.

BIHEs as described herein can be quantitatively evaluated such that their design and function can be optimized. Three domains of testing can be conducted on the BIHEs: thermal, hydraulic, and elastic. The thermal and hydraulic measurements can be performed on a test rig that is designed to replicate the thermal load that may be imposed on a medical heat exchanger in contact with glabrous skin having a high rate of blood flow through the AVA network. The experimental test rig is shown in FIG. 4. Test rig components include: a ⅛" glass plate that simulates the thermal impedance of glabrous skin; a ThermaZone thermoelectric cryotherapy system with the pad mounted on the back surface of the glass plate to simulate perfusion of blood through the AVA vasculature at a controlled temperature (usually regulated between 36 and 37° C.); a programmable system to circulate water though a test pad applied to the front side of the glass plate with water temperature regulated between 4 and 50° C. and at controlled volume flow rates up to 1 l/min; accurately calibrated instrumentation to monitor multiple temperatures, pressures, flow rates, and heat fluxes at strategic locations throughout the apparatus; analog to digital (A/D) components for data acquisition and logging into a host computer; and insulation placed over all external surfaces to thermal isolate the testing process from parasitic heat transfer with the environment. The experiments are all run in conjunction with existing instrumentation and analysis systems. The net heat exchange of a BIHE is calculated as the differential in enthalpy entering and leaving the BIHE via the volume flow rate of water and inlet and outlet temperatures. Local surface heat flux is monitored via a transducer on the glass plate. The pressure drop across a BIHE is determined by transducers at the inlet and outlet. The source pump is programmable so that pulsatile flow effects may be tested as well as transient behaviors. Pulse rates will be no faster than a few Hz. Accordingly, in some implementations, the BIHE (e.g., heat exchange pad 100 of FIGS. 1A and 1B) can further include a pulsating flow source fluidly connected to the BIHE inlet. Alternatively or additionally, the BIHE can further include a deformable member arranged within the internal volume. The deformable member can be configured to generate pulsatile flow. As described herein, pulsatile flow can be advantageous for improving heat exchange.

Figure 5:
FIG. 5 illustrates progressive uniform filling of a 233 microchannel BIHE with colored water. The inlet manifold is on the top right and the outlet manifold is on the top left in FIG. 5.

Dedicated trials can be run for each BIHE prototype iteration and each control heat exchange pad to be evaluated with a full set of instrumentation employed. Four replicate trials can be conducted for each design to define a statistical basis for variations in fabrication. Standard flow visualization methods can be used to determine fluid movement patterns and uniformity through the BIHE. Initial studies on BIHE prototypes as shown in FIG. 5 indicate that the flow is spread very uniformly through the microchannel network (e.g., the fluid conduits and/or headers) of a BIHE. A few of the flow shunts in FIG. 5 are not filled due to residual 3-D printed mold material not being cleared, but fabrication methods can be improved to resolve this issue.

Thermal imaging can be used to measure the two dimensional homogeneity of the temperature on the BIHE surface, as seen in FIGS. 6A and 6B. Pattern quantification of the thermal variations across the BIHE surface is accomplished with standard image analysis software. Thermal performance of the BIHE is critically dependent on the thermal conductivity of the body material. The overall thermal conductivity through the fabricated BIHE body can be measured using the test rig. Water heated and cooled brass cylinders with diameters substantially smaller than the lateral dimension of the BIHE can be placed above and below the device to impose a longitudinal heat flow, with a heat flux gauge at the high temperature surface. The entire apparatus can be insulated against environmental heat leaks. Temperatures can be held in the range between 5 and 50° C. and monitored at the BIHE warm and cool interfaces. Conductivity can calculated with a Fourier's law equations as a function of the heat flux, two interface temperatures, cylinder cross sections, and BIHE thickness.

The elastic loading required to deform a BIHE around a curved surface can be measured in terms of the tensile force applied to a flexible band to conform the device to a cylinder of specific diameter, as illustrated in FIGS. 7A and 7B. Note that although the BIHE is strongly deformed, the structural integrity of the internal microchannels is maintained, resulting in a uniform temperature distribution on the surface. As shown in FIGS. 7A and 7B, there are no areas that become starved for water flow when the BIHE is bent to an angle that approximates anatomical joint geometries such as the knee and shoulder. The force required to conform the BIHE can be monitored with a digital tensiometer with the signal output directly via the A/D interface to a host computer. Tests can be performed on spherical as well as cylindrical surfaces. BIHE prototypes can be deformed at 0, 45, and 90 degree orientations to the primary flow axis through the interior channels to evaluate the effect of specific moments of inertia associated with different microchannel structures. The bending force will also be measured for incremental interior water pressures that can influence overall rigidity. Conventional medical heat exchangers become significantly stiffened as the interior pressure increases. In contrast, the BIHEs described herein are quite resistant to this stiffening.

BIHE designs can be compared for thermal, hydraulic and elastic performance with examples of commercial welded polymer sheet water flow cooling pads for which there are two distinct styles: serpentine and bladder volume with interspersed spot welds (Khoshnevis et al, 2014). These will be randomly selected (a total of 2) to serve as controls. G*Power version 3.1 was used to calculate the number of replicate BIHE needed for testing, based on simulation results to define the degree of variability for each measurement metric in comparison to the controls. A sample size of 4 for each group is anticipated to satisfy a significance of 0.05 and the power of 0.95. Exemplars of each BIHE design will be tested and compared with the others and with the controls for performance in heat exchange, fluid flow, and bending. One-way analysis of variance (ANOVA) can be used to compare the outcome of each metric among the different pads. Significance will be set at 0.05.

Performance of the BIHE designs can be evaluated in comparison with two standards. The first standard is the temperature pads for existing thermal therapy devices. These tend to have high flexibility and low thermal performance. The second standard is microchannel water flow heat exchangers designed for microelectronics. These tend to have high thermal performance, but are totally rigid and unable to conform to complex anatomies. These measurements can all be performed on tissue surrogate test rig. The BIHE can also be adapted to testing of therapeutic devices on human subjects, especially on glabrous skin under conditions of vasodilation.

Based on AVA anatomical dimensions, the size the individual BIHE modules will be relatively small compared to the total heat transfer area at typical treatment sites. Therefore, a linking header system can be used to couple multiple BIHE modules to achieve anatomical total sizes. Evaluations indicate that flexible coupling can be used to link a plurality of BIHE modules. Alternatively or additionally, this disclosure contemplates that continuous improvements in 3-D printing technology coupled with reduced costs of device systems and raw materials will result in fabrication of larger BIHEs. The performance requirements of the BIHE require optimization in design across competing qualities. Thus, several different designs of the BIHE can be developed, each with its own combination of strengths and limitations.

Finite element simulations can be used to analyze the combined thermal, hydraulic and elastic operational characteristics of BIHE designs. Meshing of specific device and anatomical geometries can be accomplished with software from AUTODESK, INC of San Rafael, Calif., in some cases using a shared database from the files applied to direct the 3-D printing process for microchannel flow geometries. For example, simulation calculations can be carried out via ANSYS CFD software run on a dedicated supercomputer. The simulation model is a tool to perform sensitivity analyses for BIHE performance as key properties are varied, obviating time-consuming manufacturing and testing with physical models. Incremental values of key properties can be used in the model to simulate thermal, hydraulic and/or elastic performance while a BIHE is pressurized with flowing water. The environment will be blood perfused glabrous skin. The simulations can be used to inform BIHE design features and to provide a quantitative platform for evaluation of data obtained during testing and comparison of BIHE prototypes. The simulations can be of particular value for optimizing competing design features. For example, flow configurations that perform better for heat transfer often result in greater pressure loss of flow and vice versa (Haller et al, 2009).

Figure 8A:
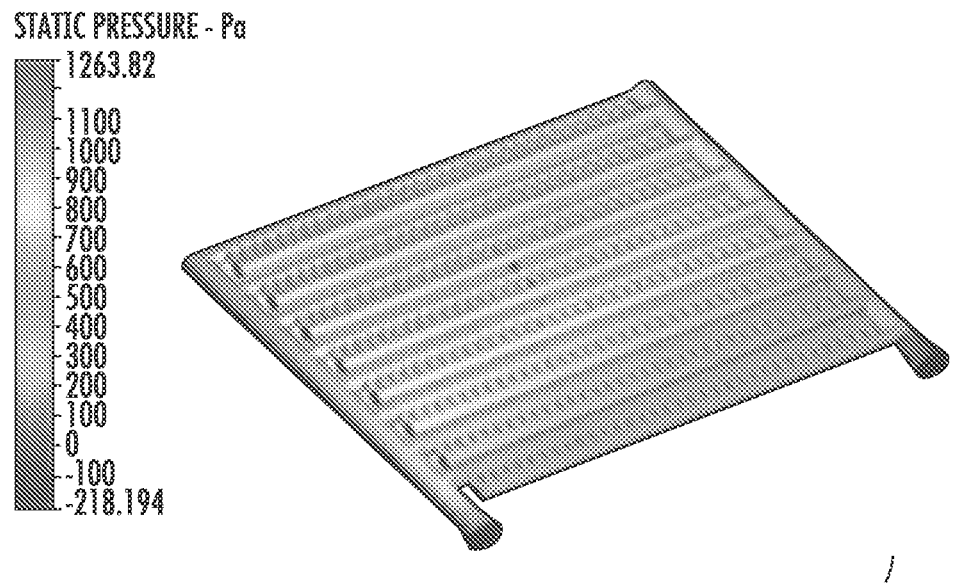
FIGS. 8A and 8B illustrate finite element modelling (FEM) simulation of the hydraulic and thermal function of the example BIHE shown in FIGS. 2A and 2B. The BIHE includes 264 microchannels or fluid conduits.
Figure 8B:
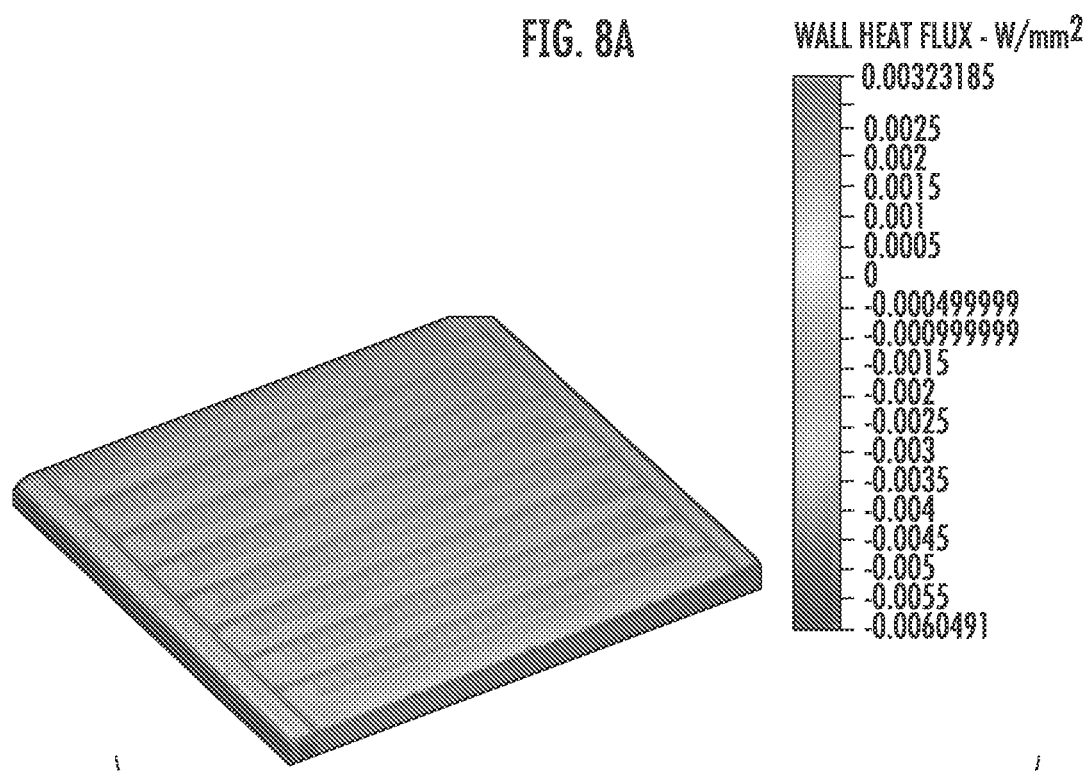
Figure 9A:
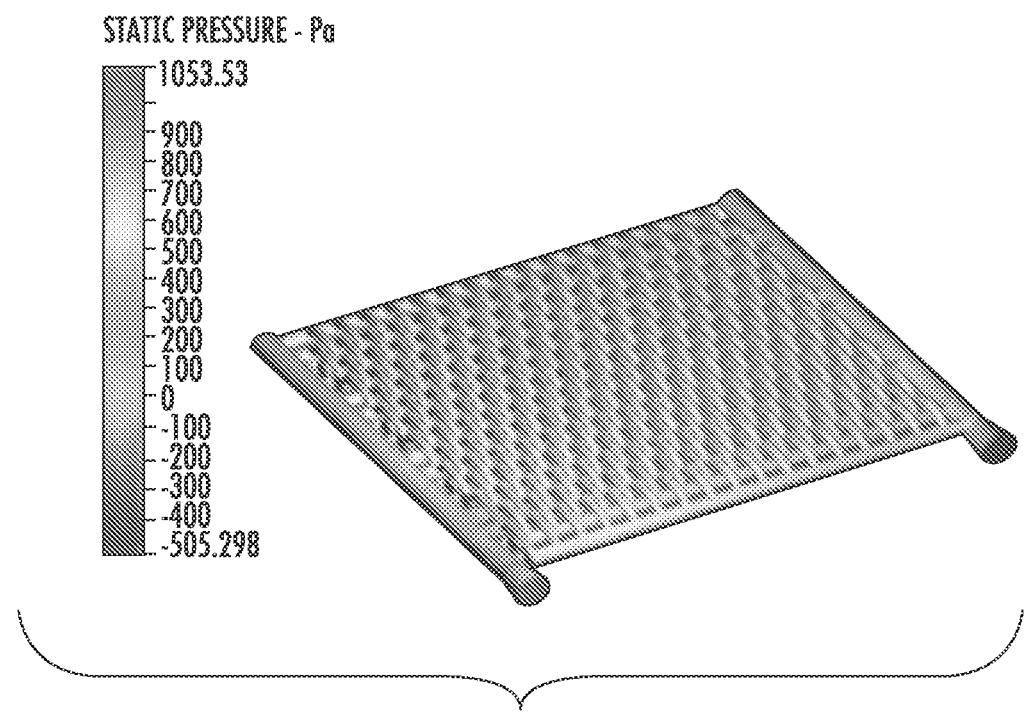
FIGS. 9A and 9B illustrate FEM simulation of the hydraulic and thermal function of the BIHE when the shunts are lengthened to bridge across alternate delivery and collection headers. The BIHE includes 231 microchannels or fluid conduits. The microchannels or fluid conduits in FIGS. 9A and 9B are longer than those in FIGS. 8A and 8B.
Figure 9B:
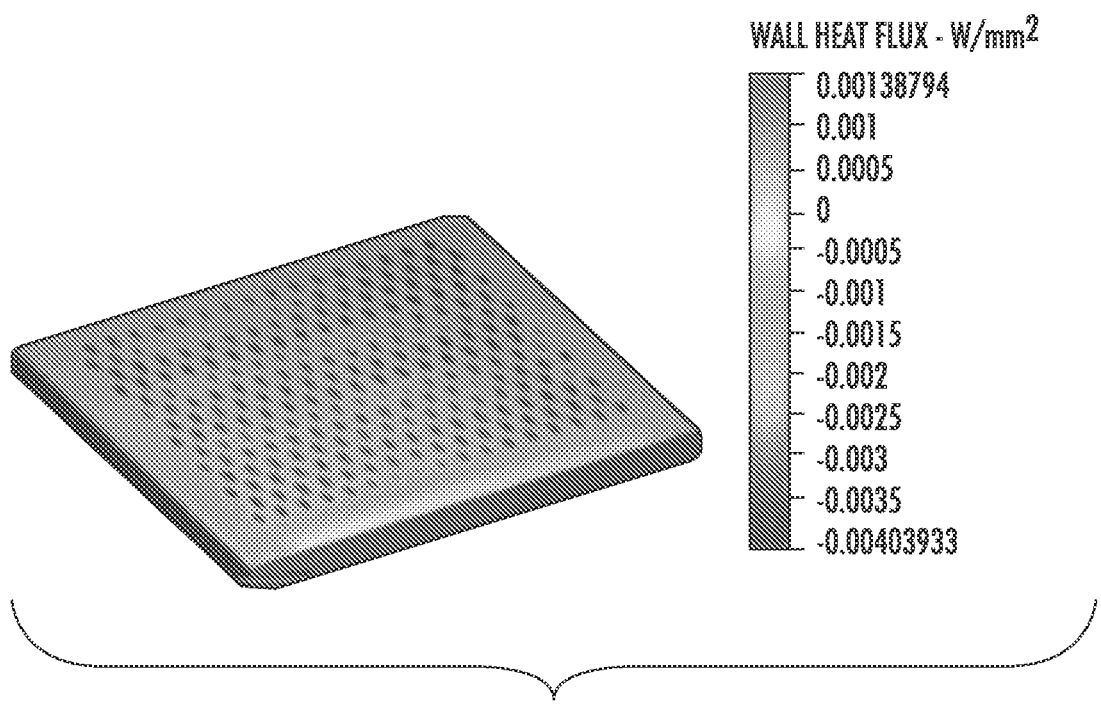

Several examples illustrate the insights that may be derived from the simulations. The BIHE shown in FIGS. 2A and 2B was meshed, and the heat transfer and fluid flow performance determined for incremental operating conditions. FIGS. 8A and 8B show the progressive pressure drop as water flows through the exchanger and the temperature distribution on the active exchange surface. To illustrate the power of exploring design iterations by simulation, FIGS. 9A and 9B present an analysis of the BIHE in which the shunt loops were restructured to be individually longer but fewer in number. The number of shunts is reduced from 264 in FIGS. 8A and 8B (with shorter shunts) to 231 in FIGS. 9A and 9B (with longer shunts). FIGS. 10A and 10B show an analysis of an equal size serpentine exchanger with a single large flow channel combined with a very thin wall. This 3-D printed serpentine heat exchanger is much more effective than conventional medical devices, in large part because a much larger portion of the total surface area has active heat transfer (Khoshnevis et al, 2014).

The FEM simulations provide quantitative comparisons between three design options. FIG. 6A shows that the pressure drop across a single flow serpentine device is much higher than for a BIHE. This is not surprising since the mammals have evolved to move blood effectively through the vascular system, including executing convective heat transfer especially in the AVAs of glabrous skin. For a common volume flow rate through the three exchangers, the pressure drop through the two versions of BIHE is 18 fold less than the serpentine exchanger. The net geometric flow resistance ($1/D^4/n$) through the BIHE network is more than three fold less than through the single serpentine channel. If the volume flow rates through the exchangers are adjusted so that all net pressure drops are equal, the flow rates through the BIHE are approximately five times larger than through the serpentine exchanger.

Differences in heat transfer performance were also simulated. The context is that traditional water flow medical heat exchangers typically can produce energy flows in the range of 30-400 $W/m^2K$. All of the simulated exchangers in FIGS. 8A-10B can be considered as microchannel devices in comparison to the existing technologies. A standard heat transfer footprint and temperature difference of 8° C. to the environment was supplied for all designs. A sensitivity analysis was used to assess the effect of thermal conductivity of the exchanger body material at 0.3, 1, 3, and 10 W/mK. The performance of the BIHE and serpentine exchangers increase in proportion to the conductivity of the material eventually reaching a value of 4,700 $W/m^2K$. The BIHE in FIGS. 8A and 8B has a modest advantage over that of FIGS. 9A and 9B because it has a larger number of shunt microchannels. However, there should be an optimization point between increasing the number of shunts and increasing the length of individual shunts. Optimizing this type of design feature can be performed as described above, for example using FEM.

Compared to the traditional heat exchanger pads, even for the worst case BIHE at least match the very best of the existing performance level. As the thermal conductivity of the body material increases, the BIHE thermal performance becomes increasingly differentiated from the serpentine type design, eventually becoming two fold better. This behavior is a consequence of the BIHE having superior internal convective heat transfer properties so that as thermal diffusion through the exchanger becomes less of a limiting factor (Biot number increasing), the performance advantage of the BIHE becomes stronger.

The simulations described herein illustrate the power and benefit of finite element modeling to explore and evaluate a large array of options in the design and evaluation of microchannel BIHEs. There are many additional design features that can be studied beyond those presented herein. For example, the 3-D printing fabrication method allows complex structures interior to the flow channel to be created as well as prescribed surface roughness, all for enhancement of fluid mixing and improved convection. This effect is particularly important for the low Reynolds number (Re) flows that characterize microchannel exchangers. It is anticipated that the BIHE will have Re less than a few hundred. There are many options for the size, shape, spacing, and orientation of internal mixing structures, surely more that should reasonably be fabricated and tested. FEM simulation provides an effective platform for screening options to determine the most promising design candidates for physical fabrication and testing.

FEM simulations are also well suited to determining the effects of the internal channel pattern and the levels of internal pressure of water circulating therein on the BIHE ability to conform to anatomical curved surfaces. Extensive past studies on conventional medical heat exchangers have demonstrated that the interior flow pattern and pressure exert a strong effect on the ability of a heat exchanger to match a body contour and to maximize the surface contact area to achieve full heat transfer communication at a treatment site. The FEM has long been recognized as an excellent tool for performing analyses of the elastic properties of complex structures. It is important to assess not only the bending strength both also the threshold conditions under which internal channels will begin to collapse, leading to restrictions in flow and compromised convection heat transfer.

The BIHEs described herein can be of direct benefit to society in terms of diverse medical applications ranging from treatment of events such as stroke, cardiac arrest and concussion that deprive the brain of oxygen, to providing for new thermal therapies for more effective healing of soft tissue wounds associated with surgery and diverse injuries and accidents. It is anticipated that the BIHE technology described herein will find novel applications that cannot be predicted.

Figure 13A:
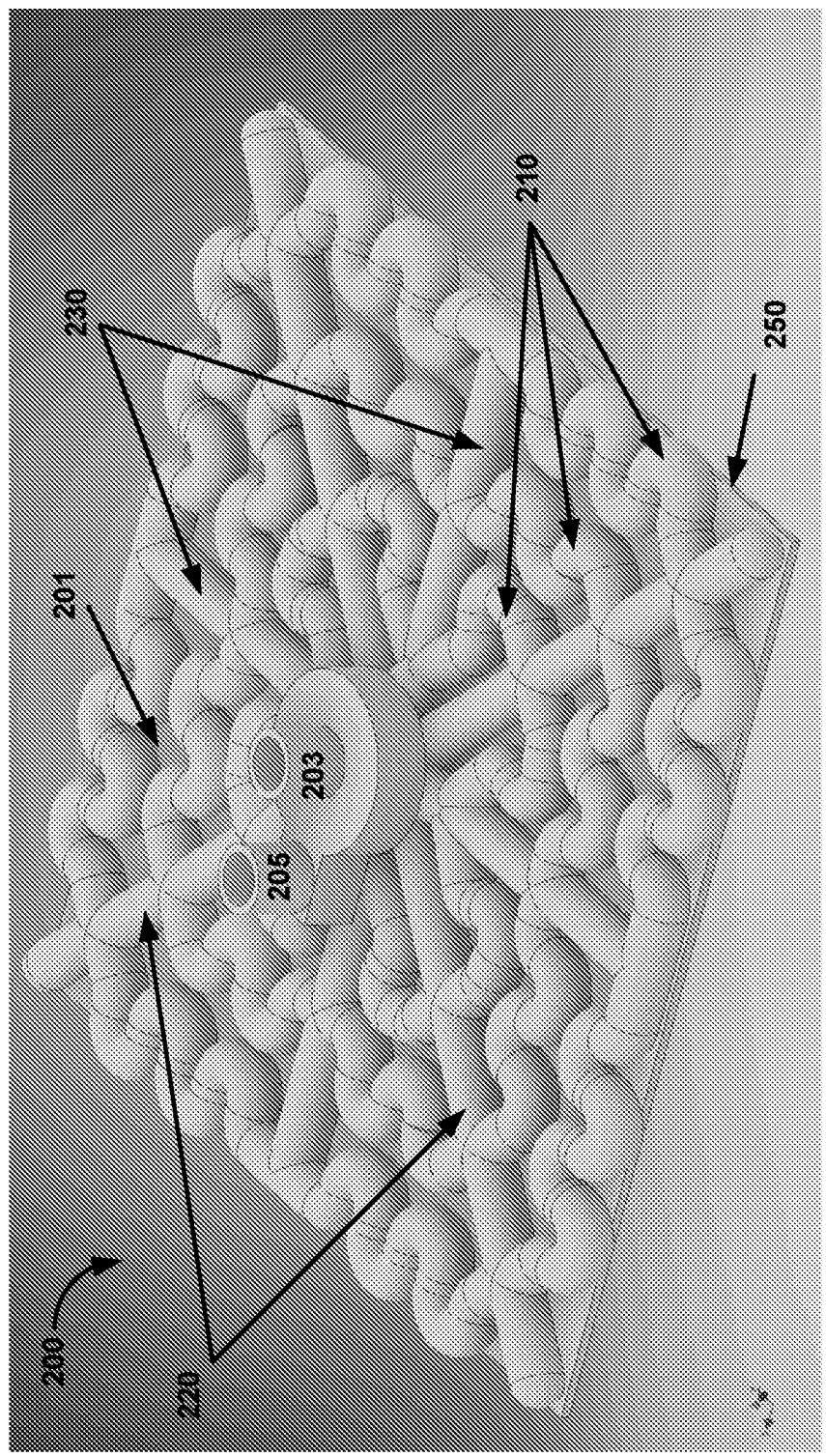
FIGS. 13A-13C illustrate another example 3-D printed biologically-inspired heat exchanger (BIHE) according to an implementation described herein.
Figure 13B:
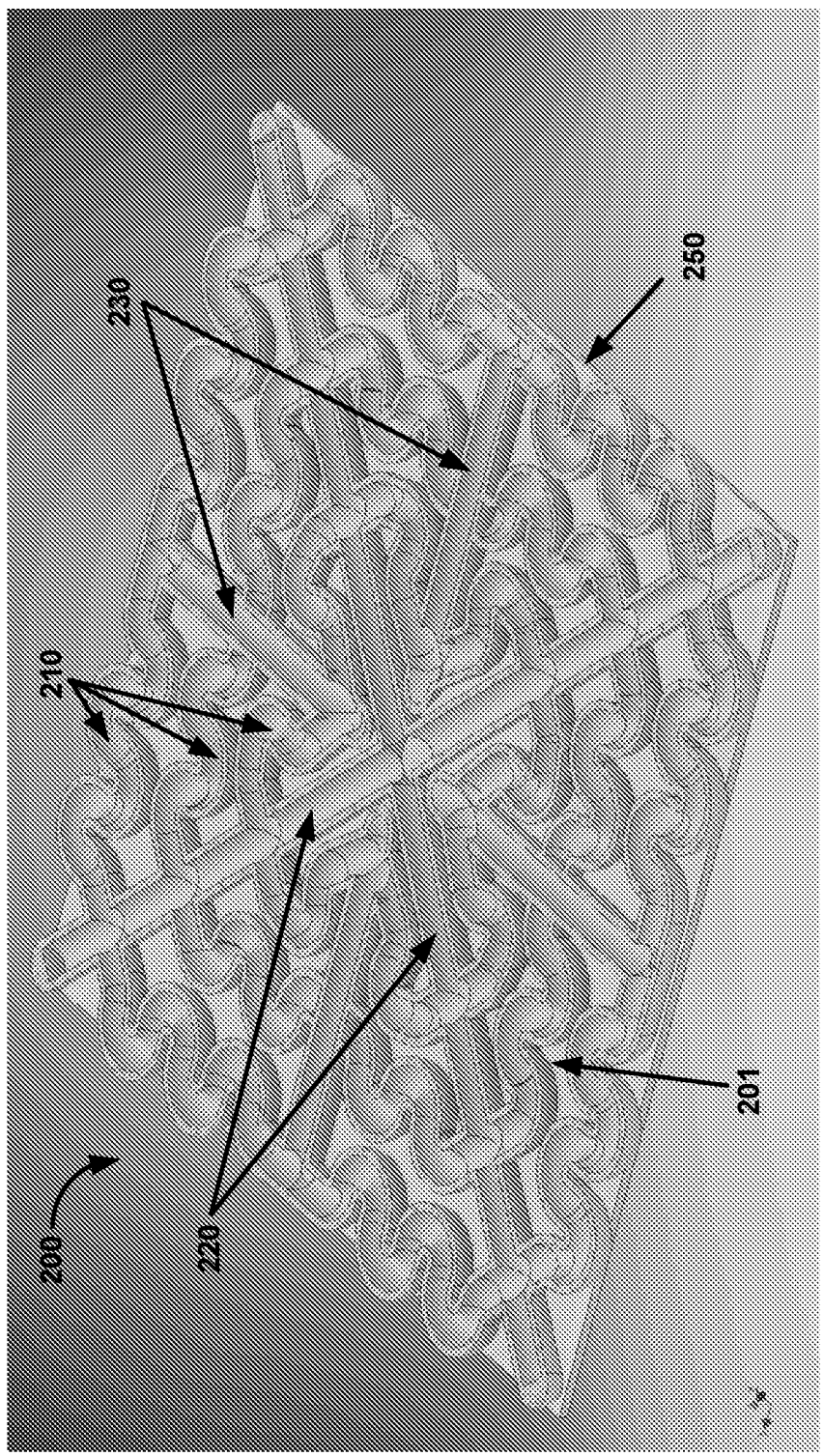
Figure 13C:
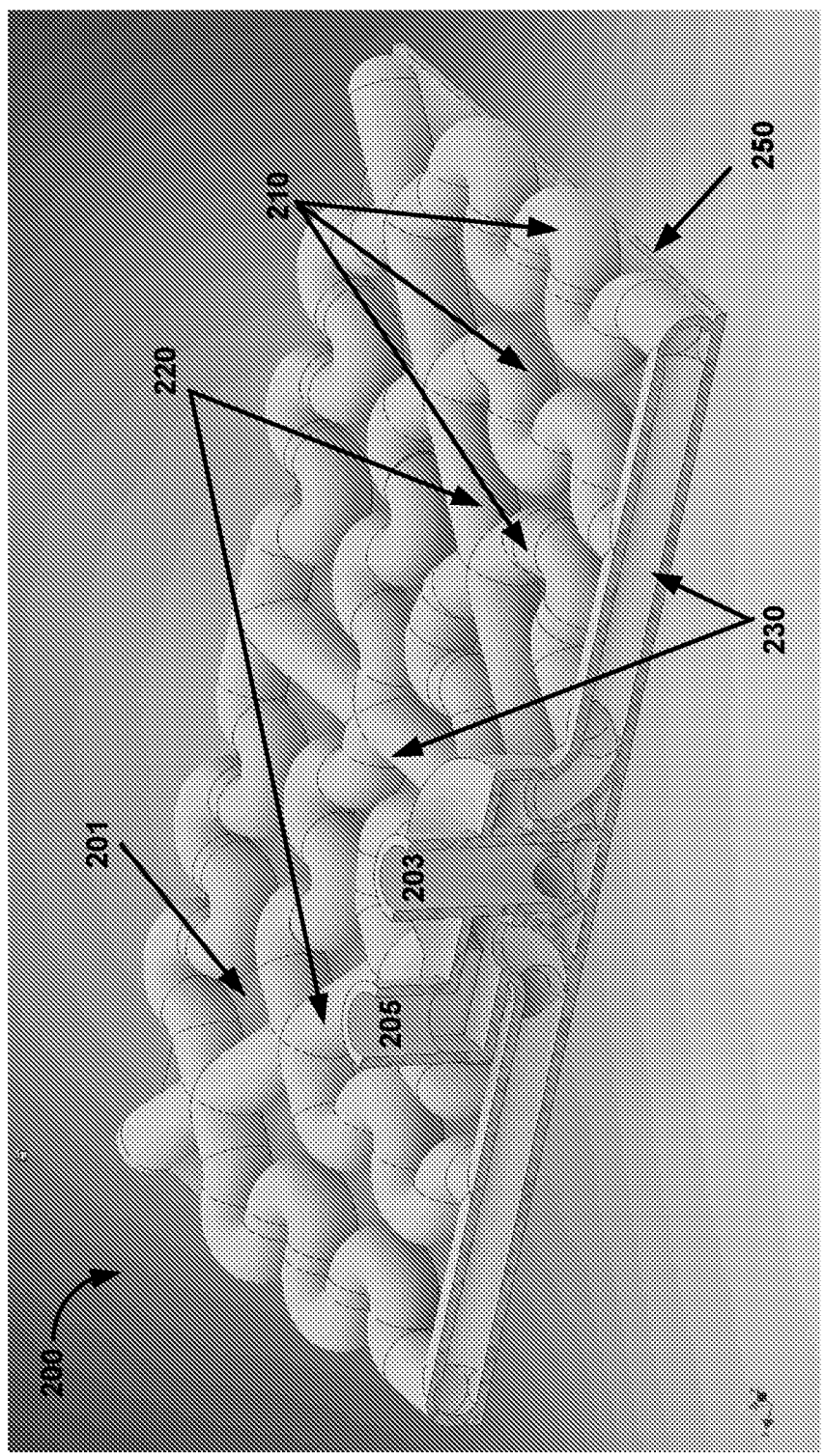

Referring now to FIGS. 13A-13C, another example 3-D printed BIHE is described. FIGS. 13A-13C illustrate a central vascular design. The BIHE, which is referred to as a heat exchange pad 200, is based on the vascular anatomy and thermal function of blood flow through the networks of AVAs in glabrous skin. As discussed above, the features of the heat exchange pad 200 mimic AVAs in tissue (e.g., elastic deformability; flow channel density per volume; channel diameter, length, shape, tortuosity, and spacing; and vortex generator structure geometry). For example, AVA structure consists of a tight tangle of vessels positioned below the surface of the dermis. AVAs function as flow shunts between the arterioles and venules, allowing blood to bypass the nutritive network of capillaries. AVAs form a highly dense network of flow conduits having tortuous shapes that enhance convective heat exchange with the blood.

The heat exchange pad 200 can include a surface defining an internal volume 201 and having a flexible patient contacting portion 250, an inlet 203 fluidly connected to the internal volume 201 for delivery of fluid into the internal volume 201, an outlet 205 fluidly connected to the internal volume 201 for removal of fluid from the internal volume 201, and at least one extended surface structure 210 positioned within the internal volume 201 to disrupt laminar flow of fluid from the inlet 203 to the outlet 205. As discussed above, the heat exchange pad 200 can be configured to mimic a vascular structure of glabrous skin tissue. The at least one extended surface structure 210 can be configured with a shape irregularity (e.g., a sharp turn and/or change in cross sectional diameter as described herein).

As shown in FIGS. 13A-13C, the at least one extended surface structure 210 includes a plurality of fluid conduits. The fluid conduits are arranged to guide fluid between a delivery header 220 and a collector header 230. The delivery and collector headers 220 and 230 are in fluid connection with the inlet 203 and outlet 205, respectively. Additionally, in FIGS. 13A-13C, the fluid conduits spiral outward from a central region of the heat exchange pad 200. In other words, the fluid conduits branch outward from the central region of the heat exchange pad 200 and move fluid between the delivery and collector headers 220 and 230. The fluid conduits of the at least one extended surface structure 210 are coil-like in design (e.g., tortuous flow, shape irregularities, optionally with varying internal diameter). This allows the fluid conduits to be act as springs or coils, which provides advantages. For example, the fluid conduits allow the heat exchange pad 200 to deform in almost any direction without major distortion to inside flow diameter. This is due to the centralized coiled design. Additionally, this design makes the heat exchange pad 200 act more like a spring in the sense that the areas are more likely to unfold than stretch and deform. In other words, the coiled fluid conduits of the at least one extended surface structure 210 tend to unfold as opposed to stretch and deform. This makes the heat exchange pad 200 more flexible. The heat exchange pad 200 can therefore be wrapped around more complex anatomy without distorting flow within the heat exchange pad 200. Optionally, the heat exchange pad 200 can be modular. For example, one or more of the quadrants shown in FIG. 13A can be modular and can be attachable to/detachable from the heat exchange pad 200 itself. This can be accomplished by connections between one or more of the fluid conduits of the at least one extended surface structure 210 and/or the delivery and collector headers 220 and 230.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A heat exchange pad for use on a patient, comprising:
    a surface defining an internal volume and having a flexible patient contacting portion;
    an inlet fluidly connected to the internal volume for delivery of fluid into the internal volume;
    an outlet fluidly connected to the internal volume for removal of fluid from the internal volume; and
    a microchannel network comprising at least one extended surface structure positioned within the internal volume to disrupt laminar flow of fluid from the inlet to the outlet, wherein:
    the at least one extended surface structure comprises a plurality of coiled fluid microchannels,
    each of the coiled fluid microchannels is a discretely defined geometric channel defining a pathway to a plurality of delivery headers and a plurality of collector headers, and
    the microchannel network is configured to mimic a vascular network by branching outward from a central region of the heat exchange pad to move fluid between the plurality of delivery headers and the plurality of collector headers.

2. The heat exchange pad of claim 1, wherein the heat exchange pad is configured to mimic a vascular network structure of glabrous skin tissue.

3. The heat exchange pad of claim 1, wherein the at least one extended surface structure is configured with a shape irregularity.

4. The heat exchange pad of claim 1, wherein the coiled fluid microchannels are configured to enhance convective heat transfer.

5. The heat exchange pad of claim 1, wherein at least one of the coiled fluid microchannels has a tortuous flow path.

6. The heat exchange pad of claim 1, wherein at least one of the coiled fluid microchannels has a varying inner diameter.

7. The heat exchange pad of claim 1, wherein each of the plurality of delivery headers is fluidly connected to the inlet and each of the plurality of collector headers is fluidly connected to the outlet, wherein the coiled fluid microchannels are arranged to guide fluid between the plurality of delivery headers and the plurality of collector headers.

8. The heat exchange pad of claim 1, wherein a length of at least one of the coiled fluid microchannels is substantially less than a length of the heat exchange pad.

9. The heat exchange pad of claim 1, wherein a length of the at least one extended surface structure is substantially greater than a length of the heat exchange pad.

10. The heat exchange pad of claim 1, wherein a ratio of an internal convection area to an external convention area is greater than 3:1.

11. The heat exchange pad of claim 1, wherein the surface, the inlet, the outlet, and the at least one extended surface structure comprise a unitary structure.

12. The heat exchange pad of claim 11, wherein the unitary structure is a contiguous three-dimensional structure.

13. The heat exchange pad of claim 11, wherein the unitary structure is configured to withstand greater than 2.0 atmospheres of internal pressure.

14. The heat exchange pad of claim 1, wherein the flexible patient contacting portion of the surface is configured to elastically conform to the patient's anatomy.

15. The heat exchange pad of claim 1, further comprising a pulsating flow source fluidly connected to the inlet.

16. The heat exchange pad of claim 1, further comprising a deformable member arranged within the internal volume, wherein the deformable member is configured to generate pulsatile flow.

17. The heat exchange pad of claim 1, further comprising a fluid flowing through the internal volume, wherein the fluid comprises nanoparticles configured to enhance heat transfer.

18. A system, comprising:
    a plurality of heat exchange pads as claimed in claim 1, wherein the heat exchange pads are fluidly connected through the inlets and outlets thereof.

19. The heat exchange pad of claim 1, wherein the discretely defined geometric channel has a tubular shape.

20. The heat exchange pad of claim 1, wherein a ratio of a length to an inner diameter of each of the plurality of coiled fluid microchannels is between 6:1 and 10:1.

\* \* \* \* \*